United States Patent
Sauer et al.

(10) Patent No.: US 11,458,200 B2
(45) Date of Patent: Oct. 4, 2022

(54) CONSTRUCTS, AGENTS, AND METHODS FOR FACILITATED ABLATION OF CARDIAC TISSUE

(71) Applicants: William Sauer, Newton, MA (US); Duy Nguyen, Palo Alto, CA (US)

(72) Inventors: William Sauer, Newton, MA (US); Duy Nguyen, Palo Alto, CA (US)

(73) Assignee: William Sauer, Newton, MA (US)

( * ) Notice: Subject to any disclaimer, the term of this patent is extended or adjusted under 35 U.S.C. 154(b) by 542 days.

(21) Appl. No.: 16/099,108

(22) PCT Filed: May 4, 2017

(86) PCT No.: PCT/US2017/030975
§ 371 (c)(1),
(2) Date: Nov. 5, 2018

(87) PCT Pub. No.: WO2017/192804
PCT Pub. Date: Nov. 9, 2017

(65) Prior Publication Data
US 2019/0328877 A1     Oct. 31, 2019

Related U.S. Application Data

(60) Provisional application No. 62/331,745, filed on May 4, 2016.

(51) Int. Cl.
*A61K 41/00*     (2020.01)
*A61B 18/02*     (2006.01)
(Continued)

(52) U.S. Cl.
CPC .......... *A61K 41/0028* (2013.01); *A61B 18/02* (2013.01); *A61B 18/1492* (2013.01);
(Continued)

(58) Field of Classification Search
CPC .. A61K 41/0028; A61K 33/244; A61K 9/127; A61K 9/5115; A61K 31/366;
(Continued)

(56) References Cited

U.S. PATENT DOCUMENTS 6,416,510 B1 *   7/2002   Altman .............. A61B 18/1492
                                                 606/41
7,819,795 B1 *   10/2010   Seeney ................ H04R 25/606
                                                 600/25
(Continued)

FOREIGN PATENT DOCUMENTS

WO    WO 2011/049680 A1    4/2011
WO    WO 2015/164857 A1    10/2015

OTHER PUBLICATIONS

Notification Concerning Transmittal of International Preliminary Report on Patentability, PCT/US2017/030975, dated Nov. 15, 2018, 9 pages.
(Continued)

*Primary Examiner* — Lauren P Farrar
*Assistant Examiner* — Hamza A Darb
(74) *Attorney, Agent, or Firm* — David G. Rosenbaum; Rosenbaum IP

(57) ABSTRACT

The presently disclosed subject matter provides agents, compositions, and methods for augmenting ablation of a target tissue in a subject in need thereof, for example, using agents that modulate protective and/or reparative cellular processes induced in target tissue by application of ablative energy to the target tissue to sensitize the target tissue to the ablative energy. The presently disclosed subject matter further provides methods for augmenting radiofrequency ablation of cardiac tissue, for example, by applying radiofre-
(Continued)

quency energy to ablate cardiac tissue in the presence of metallic nanoparticles magnetically guided to the cardiac tissue.

18 Claims, 5 Drawing Sheets

(51) Int. Cl.

| | | |
|---|---|---|
| A61B 18/14 | (2006.01) | |
| A61B 18/00 | (2006.01) | |
| A61K 9/127 | (2006.01) | |
| A61K 9/51 | (2006.01) | |
| A61K 31/366 | (2006.01) | |
| A61K 33/244 | (2019.01) | |
| A61K 33/26 | (2006.01) | |
| A61K 45/06 | (2006.01) | |
| A61K 49/18 | (2006.01) | |
| A61N 2/00 | (2006.01) | |
| A61P 41/00 | (2006.01) | |

(52) U.S. Cl.
CPC ............ *A61K 9/127* (2013.01); *A61K 9/5115* (2013.01); *A61K 31/366* (2013.01); *A61K 33/244* (2019.01); *A61K 33/26* (2013.01); *A61K 41/00* (2013.01); *A61K 45/06* (2013.01); *A61K 49/1818* (2013.01); *A61N 2/002* (2013.01); *A61P 41/00* (2018.01); *A61B 2018/00351* (2013.01); *A61B 2018/00577* (2013.01)

(58) Field of Classification Search
CPC ........ A61K 33/26; A61K 41/00; A61K 45/06; A61K 49/1818; A61K 31/352; A61K 41/0038; A61P 41/00; A61B 18/02; A61B 18/1492; A61B 2018/00351; A61B 2018/00577; A61B 34/73; A61B 2018/1472; A61N 2/002; A61N 7/00
See application file for complete search history.

(56) References Cited

U.S. PATENT DOCUMENTS

| | | |
|---|---|---|
| 8,951,527 B2 | 2/2015 | Isenberg et al. |
| 2012/0095442 A1 | 4/2012 | Dormer et al. |
| 2012/0143167 A1 | 6/2012 | Morrison et al. |

OTHER PUBLICATIONS

Notification of Transmittal of the International Search Report and the Written Opinion, PCT/US17/30975, dated Aug. 2, 2017, 13 pages.

Nguyen et al., "Gadolinium Augmentation of Myocardial Tissue Heating During Radiofrequency Abation," JACC: Clinical Electrophysiology, vol. 1, No. 3, Jun. 2015, pp. 177-184.

Yang et al., "Radiofrequency ablation combined with liposomal quercetin to increase tumour destruction by modulation of heat shock protein production in a small animal model," Int. F. Hyperthermia, vol. 27, No. 6, Sep. 2011, pp. 527-538.

\* cited by examiner

CONSTRUCTS, AGENTS, AND METHODS FOR FACILITATED ABLATION OF CARDIAC TISSUE

RELATED APPLICATION DATA

This application claims the benefit of priority from U.S. Patent Application Ser. No. 62/331,745, filed May 4, 2016. The contents of which are incorporated herein by reference in its entirety.

BACKGROUND

Cardiac arrhythmias, such as ventricular tachycardia (VT) and atrial fibrillation (AF), have significant morbidity and mortality, including stroke, heart failure, and sudden death. Medical therapy alone is often not successful, and radiofrequency (RF) catheter ablation has become the standard of care for the treatment of all drug refractory arrhythmias. Efficacy of catheter ablation for the treatment of arrhythmias is dependent on the ability of RF to create durable lesions; inability to render the arrhythmogenic tissue electrically inert can lead to arrhythmia recurrences. Furthermore, ablation safety is dependent on a high level of precision to avoid unintended injury to adjacent tissue. Achieving lesion durability while maintaining ablation precision remains a challenge with current technology.

Metallic nanoparticles (NPs) are metallic elements that are nano- or micro-meter in length and diameter with an exponential increase in exposed surface area compared to larger-mass equivalents. Depending on the metal, they can have unique mechanical and electrical properties that lend themselves to various potential biomedical uses.

SUMMARY

In an aspect, the presently disclosed subject matter provides a method for augmenting ablation of a target tissue in a subject in need thereof, the method comprising: (a) administering to a subject in need thereof an effective amount of an agent that modulates a protective and/or reparative cellular process induced in a target tissue by application of an ablative energy to the target tissue; and (b) applying an ablative energy to the target tissue in the subject, wherein the agent modulates the protective and/or reparative cellular process induced in the target tissue by application of the ablative energy to the target tissue, thereby increasing sensitization of the target tissue to the ablative energy, and augmenting ablation of the target tissue in the subject.

In particular embodiments, the induced protective and/or reparative cellular process comprises a cold shock response process modulated by a cold shock protein (CSP), the agent decreases the level and/or activity of a cold shock protein in the target tissue, and the ablative energy is a cryothermal energy. In particular embodiments, the induced protective and/or reparative cellular process comprises a heat shock response process modulated by a heat shock protein (HSP), the agent decreases the level and/or activity of a heat shock protein in the target tissue, and the ablative energy is a thermal energy, wherein the thermal energy is optionally selected from the group consisting of radiofrequency energy, microwave energy, ultrasound, electromagnetic energy.

In another aspect, the presently disclosed subject matter provides a method for augmenting radiofrequency ablation of a target cardiac tissue in a subject in need thereof, the method comprising: (a) administering an effective amount of a composition comprising metallic nanoparticles to a subject; (b) using a magnetic field to guide the metallic nanoparticles to a target cardiac tissue to be ablated in the subject; and (c) applying a radiofrequency energy to the target cardiac tissue in the presence of the metallic nanoparticles guided to the target cardiac tissue, thereby augmenting radiofrequency ablation of the target cardiac tissue in the subject.

In particular embodiments, the metallic nanoparticles are selected from the group consisting of copper nanoparticles, gadolinium nanoparticles, gold nanoparticles, iron nanoparticles, titanium nanoparticles, and combinations thereof. In particular embodiments, the metallic nanoparticles are selected from the group consisting of coral-shaped, cube-shaped, rod-shaped, spherical-shaped nanoparticles, tetrapod-shaped, triangular-shaped, and combinations thereof. In particular embodiments, the metallic nanoparticles are not carbon nanotubes. In particular embodiments, the metallic nanoparticles are encapsulated in liposomes. In particular embodiments, the metallic nanoparticles are encapsulated in heat-sensitive liposomes. In particular embodiments, the composition further comprises an agent that decreases the level and/or activity of a heat shock protein. In particular embodiments, the heat shock protein is selected from the group consisting of heat shock protein 60 (Hsp60), heat shock protein 70 (Hsp70), and heat shock protein 90 (Hsp90). In particular embodiments, the agent that decreases the level and/or activity of a heat shock protein is quercetin. In particular embodiments, the agent that decreases the level and/or activity of a heat shock protein is 17-AAG. In particular embodiments, the agent that decreases the level and/or activity of a heat shock protein is celestrol.

In particular embodiments, the magnetic field is generated by a magnet that exhibits a pound pull force of between 0.001 and 1000. In particular embodiments, the magnet is placed adjacent to the target tissue (e.g., cardiac tissue) to be ablated. In particular embodiments, the magnet is a rare-earth magnet. In particular embodiments, the magnet is a neodymium magnet. In particular embodiments, the radiofrequency energy is applied using an ablation catheter. In particular embodiments, the ablation catheter comprises a magnetic tip. In particular embodiments, the magnetic tip of a catheter (e.g., ablation catheter, mapping catheter, ultrasound catheter, etc.) comprises a magnet (e.g., an electromagnet that can be turned on and off) that is used to guide the metallic nanoparticles to the target cardiac tissue to be ablated. In particular embodiments, the radiofrequency energy applied is between 1 W and 100 W.

In particular embodiments, the subject: (i) has a pacemaker; and/or (ii) has an implantable cardiac defibrillator; and/or (iii) is selected for treatment of a cardiac arrhythmia selected from the group consisting of atrial fibrillation, premature atrial contractions, wandering atrial pacemaker, multifocal atrial tachycardia, atrial flutter, supraventricular tachycardia, tachycardia selected from the group consisting of atrial tachycardia, atrioventricular nodal reentrant tachycardia, and atrioventricular reciprocating tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, arrhythmogenic right ventricular dysplasia, dilated cardiomyopathy, cardiomyopathy due to prior myocardial infarction, and abnormal Purkinje potentials leading to ventricular arrhythmias including electrical storms; and combinations thereof.

In particular embodiments, a presently disclosed method includes imaging the metallic nanoparticles in the subject. In particular embodiments, a presently disclosed method includes administering an effective amount of at least one prophylactic agent to the subject to reduce the risk and/or severity of an adverse reaction to the composition administered to the subject.

In yet another aspect, the presently disclosed subject matter provides a method for treating a cardiac arrhythmia in a subject in need thereof, the method comprising (a) performing a presently disclosed method for augmenting ablation of a target cardiac tissue in the subject; and (b) applying an ablative energy to the target cardiac tissue in the subject, thereby treating the subject in need of augmented ablation of the target cardiac tissue.

In particular embodiments, the cardiac arrhythmia is selected from the group consisting of atrial fibrillation, premature atrial contractions, wandering atrial pacemaker, multifocal atrial tachycardia, atrial flutter, supraventricular tachycardia, tachycardia selected from the group consisting of atrial tachycardia, atrioventricular nodal reentrant tachycardia, and atrioventricular reciprocating tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, arrhythmogenic right ventricular dysplasia, dilated cardiomyopathy, cardiomyopathy due to prior myocardial infarction, and abnormal Purkinje potentials leading to ventricular arrhythmias including electrical storms; and combinations thereof.

In particular embodiments, the subject has a pacemaker and/or an implantable cardiac defibrillator. In particular embodiments, the method of treating the cardiac arrhythmia includes administering to the subject an effective amount of at least one antiarrhythmic agents, at least one calcium channel blocker, at least one beta-blocker, at least one anticoagulant, at least one anti-inflammatory agent, at least one anti-fibrotic agent, and combinations thereof, or administering to the subject an effective amount of at least one prophylactic agent to reduce the risk and/or severity of an adverse reaction to the composition administered to the subject.

In still other aspects, the presently disclosed subject matter provides a composition or kit comprising metallic nanoparticles and/or at least one agent that modulates a protective and/or reparative cellular process induced in a target tissue by application of an ablative energy to the target tissue.

In particular embodiments, the composition includes temperature-sensitive liposomes, the metallic nanoparticles and/or the at least one agent are encapsulated in the temperature-sensitive liposomes, and the temperature-sensitive liposomes release the metallic nanoparticles and at least one agent in the target tissue to be ablated upon exposure to a threshold temperature. In particular embodiments, threshold temperature is 40 to 50 degrees Celsius.

In particular embodiments, the kit or composition includes an effective amount of at least one prophylactic agent to the subject to reduce the risk and/or severity of an adverse reaction to the composition administered to the subject. In particular embodiments, the kit or composition comprises an effective amount of at least one antiarrhythmic agent. In particular embodiments, the kit or composition includes an effective amount of at least one calcium channel blocker. In particular embodiments, the kit or composition includes an effective amount of at least one beta-blocker. In particular embodiments, the kit or composition includes an effective amount of at least one anticoagulant. In particular embodiments, the kit or composition includes an effective amount of at least one anti-inflammatory agent. In particular embodiments, the kit or composition includes an effective amount of at least one anti-fibrotic agent.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning. A Laboratory Manual*, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange $10^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
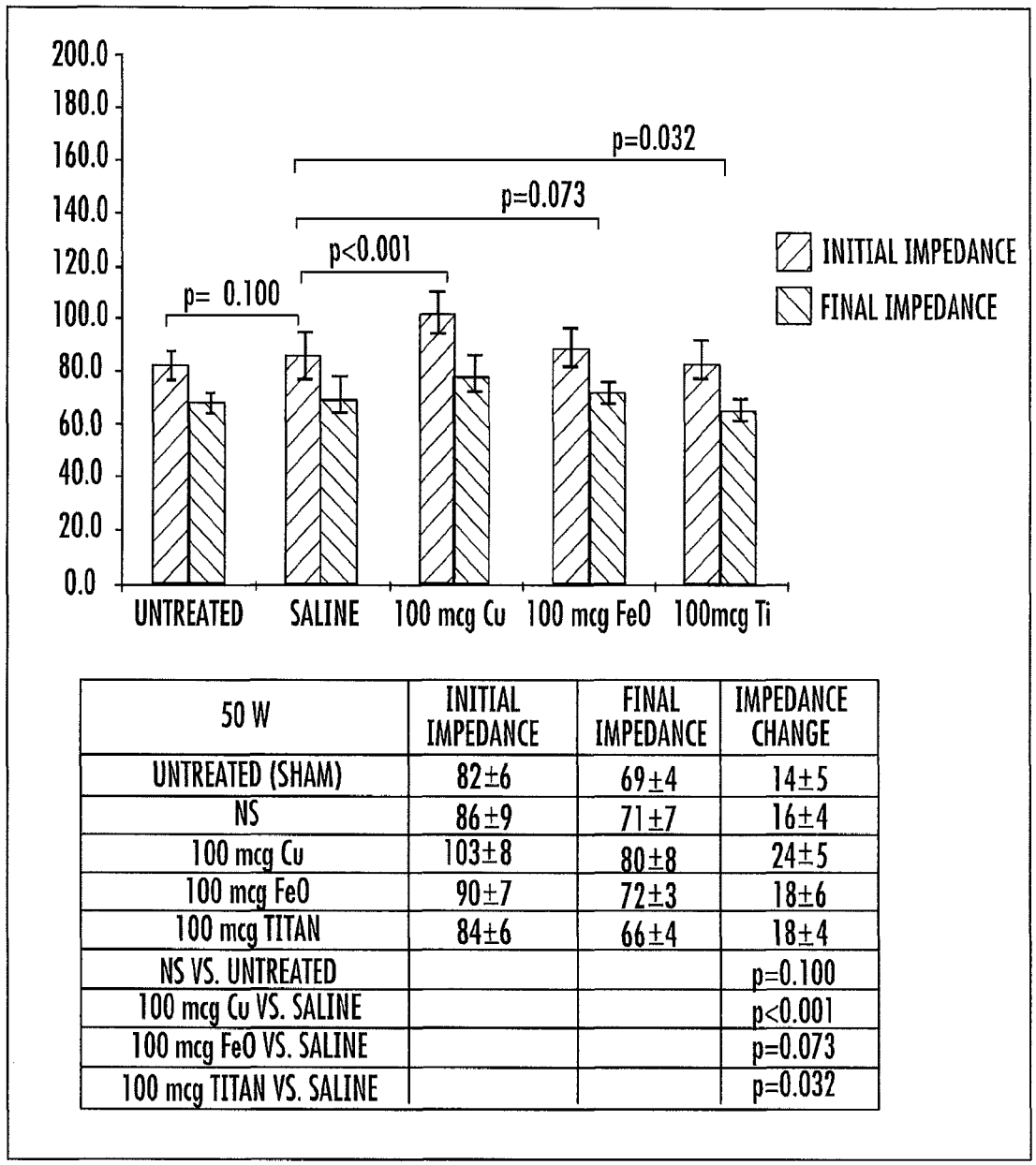
Figure 2:
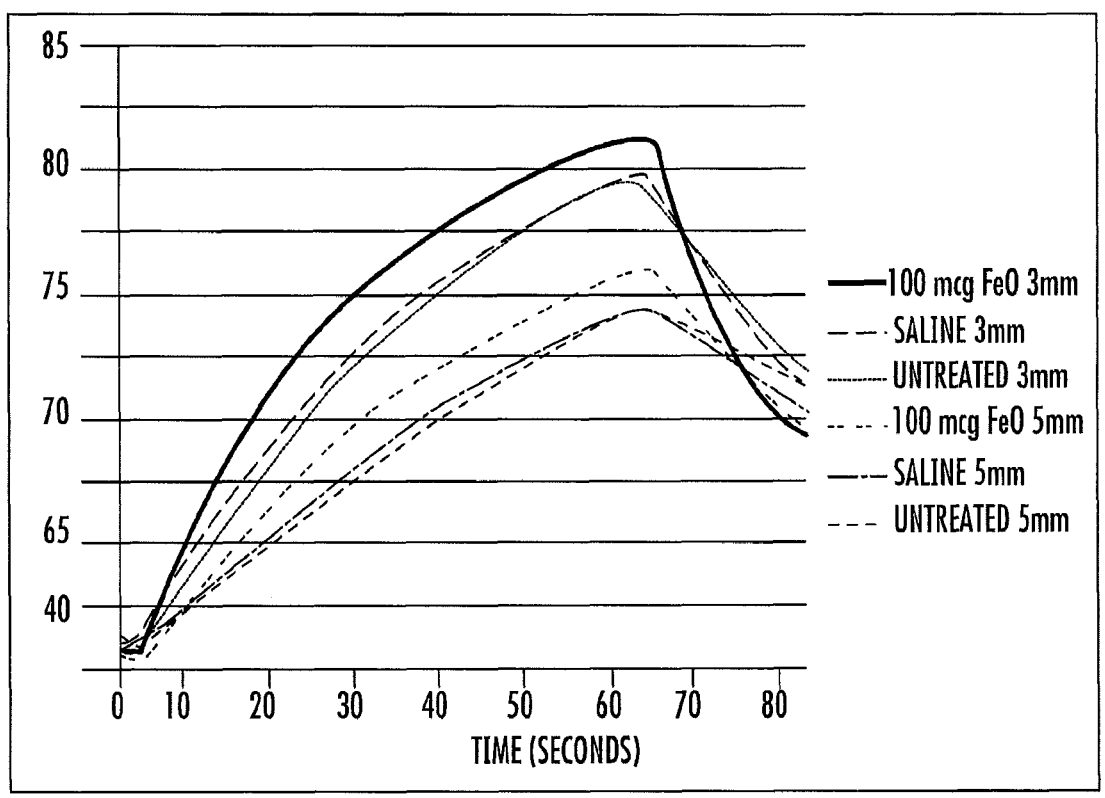
Figure 3:
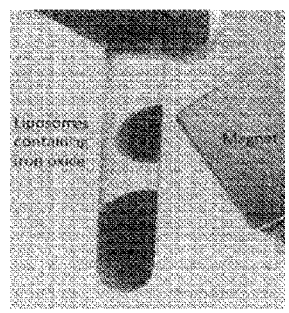
Figures 4A, 4B:
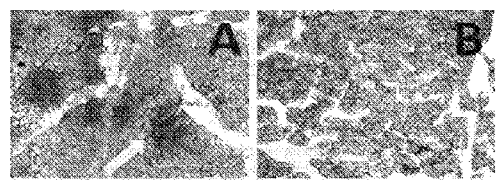
Figures 5A, 5B:
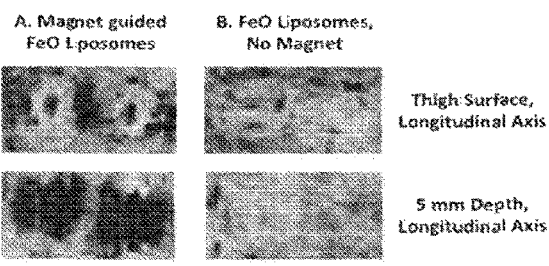

Having thus described the presently disclosed subject matter in general terms, reference will now be made to the accompanying Figures, which are not necessarily drawn to scale, and wherein:

FIG. 1 shows mean starting and ending impedance measurements in untreated control (sham), saline-infiltrated, and metal NP treated myocardial tissue before and after RF ablation at 50 W. Cu—copper. FeO—iron oxide. Ti—titanium;

FIG. 2 shows mean temperature dispersion at 3 and 5 mm depths in FeO NP treated myocardium, compared to saline infiltration or no treatment after RF at 50 Watts;

FIG. 3 shows Liposomal FeO NPs can be directed to an area of interest using magnets, as depicted in this figure, where a magnet is attracting FeO-containing liposomes against gravity;

FIG. 4A and FIG. 4B show iron staining of pathologic sections for ablated porcine thigh muscles after iron infusion (FIG. 4A) and control ablation (FIG. 4B); and FIG. 5A and FIG. 5B show MRI imaging immediately after ablation procedures shows iron deposition in the thigh preparations, which appears dark on MRI (FIG. 5A), within areas of ablation where magnets directed the iron-containing liposomes (on the surface of thigh preps and at a 5 mm depth from thigh prep surface). These dark areas were absent in areas of ablations after saline infusion (FIG. 5B).

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Modulating Induced Protective and/or Reparative Cellular Processes

The presently disclosed subject matter provides a method for augmenting ablation of target tissues (e.g., cardiac tissue). As used herein, "augmenting ablation" broadly refers increasing ablation lesion size (e.g., average maximum depth, maximum diameter, maximum surface diameter, volume, etc.), a greater reduction in electrical impedance, and/or increased thermal conductivity (e.g., increased peak temperatures in target tissue adjacent to the ablation catheter tip relative to control peak temperatures at a comparable power) in a target tissue ablated using the disclosed agents, compositions, and methods compared to ablation lesion size, reduction in electrical impedance, and/or thermal conductivity in the target tissue in the absence of using the disclosed agents, compositions, and methods, as demonstrated, for example, in the data shown in Table 1, Table 2, Table 3, and Table 4 herein, and corresponding description. In some embodiments, the agents, compositions, and methods disclosed herein created larger lesions without increasing the incidence of steam pops.

As used in some contexts herein, "augmenting ablation" refers to increasing sensitization of a target tissue to an ablative energy, for example, by modulating a cellular and/or reparative process induced by ablative energy in a target tissue that renders the target tissue to be ablated resistant to subsequent exposure to the ablative energy. In some embodiments, "augmenting ablation" improves lesion durability. In some embodiments, "augmenting ablation" enhances ablation efficiency. In some embodiments, "augmenting ablation" enhances ablation lesions using lower power ablative energy. In some embodiments, "augmenting ablation" enhances ablation lesions without requiring higher power ablative energy that is associated with complications or adverse effects to target tissue or surrounding tissue. In some embodiments, "augmenting ablation" decreases heterogeneity at the periphery of targeted tissue and myocardial infarct scar after radiofrequency energy, thereby decreasing post-ablation arrhythmia susceptibility. In some embodiments, "augmenting ablation" comprises delivering a toxin to a target tissue to be ablated (e.g., a cardiac specific toxin to a target cardiac tissue).

In an aspect, the presently disclosed subject matter provides a method for augmenting ablation of a target tissue in a subject in need thereof, the method comprising: (a) administering to a subject in need thereof an effective amount of an agent that modulates a protective and/or reparative cellular process induced in a target tissue by application of an ablative energy to the target tissue; and (b) applying an ablative energy to the target tissue to be ablated in the subject, wherein the agent modulates the protective and/or reparative cellular process induced in the target tissue by application of the ablative energy, thereby sensitizing the target tissue to the ablative energy, and augmenting ablation of the target tissue in the subject.

As used herein, "modulate", or "modulating" refer to changing the rate at which a particular process occurs, inhibiting a particular process, reversing a particular process, and/or preventing the initiation of a particular process, e.g., induction of a protective and/or reparative cellular process.

The presently disclosed subject matter contemplates any agent that modulates a protective and/or reparative cellular process induced in a target tissue by application of an ablative energy to the target tissue. Exemplary agents include, without limitation, small molecules, such as small organic or inorganic molecules; saccharides; oligosaccharides; polysaccharides; a biological macromolecule selected from the group consisting of peptides, proteins, peptide analogs and derivatives; peptidomimetics; nucleic acids, such as DNA, RNA interference molecules, selected from the group consisting of siRNAs, shRNAs, antisense RNAs, miRNAs and ribozymes, dendrimers and aptamers; antibodies, including antibody fragments and intrabodies; an extract made from biological materials selected from the group consisting of bacteria, plants, fungi, animal cells, and animal tissues; naturally occurring or synthetic compositions; and any combination thereof. In some embodiments, the agent is selected from the group consisting of small molecules, saccharides, peptides, proteins, peptidomimetics, nucleic acids, an extract made from biological materials selected from the group consisting of bacteria, plants, fungi, animal cells, and animal tissues, and any combination thereof.

As used herein, the term "small molecule" can refer to agents that are "natural product-like," however, the term "small molecule" is not limited to "natural product-like" agents. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some cases it is preferred that a small molecule.

The term "polynucleotide" is used herein interchangeably with "nucleic acid" to indicate a polymer of nucleosides. Typically a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided.

The term "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc.

As used herein, the term "antibody" refers to a polypeptide or group of polypeptides which comprise at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', $F(ab)_2$, and $F(ab')_2$ fragments.

An "RNA interfering agent" as used herein, is defined as any agent that interferes with or inhibits expression of a target gene, e.g., by RNA interference (RNAi). Such RNA interfering agents include, but are not limited to, antisense molecules, ribozymes, small inhibitory nucleic acid sequences, for example but not limited to guide RNAs, small interfering RNA (siRNA), short hairpin RNA or small hairpin RNA (shRNA), microRNA (miRNA), post-transcriptional gene silencing RNA (ptgsRNA), short interfering oligonucleotides, antisense oligonucleotides, aptamers, CRISPR RNAs, nucleic acid molecules including RNA molecules which are homologous to the target gene, or a fragment thereof, and any molecule which interferes with or inhibits expression of a target gene by RNA interference (RNAi).

In some embodiments, the agent is an RNA interfering agent. In some embodiments, the RNA is double stranded RNA (dsRNA). In some embodiments, the RNA interfering agent is a siRNA. In some embodiment, the siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In some embodiments, the RNA interference agent is a small hairpin (also called stem loop) RNA (shRNA). In some embodiments, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart et al. (2003) RNA 9:493-501).

The presently disclosed subject matter contemplates modulating any cellular and/or reparative process induced by ablative energy in a target tissue, thereby increasing the sensitization of the target tissue to the ablative energy, and augmenting the ablation of the target tissue. In some embodiments, the target tissue comprises cardiac tissue (e.g., myocardial tissue). In some embodiments, the target tissue comprises arrhythmogenic myocardial tissue. In some embodiments, the target tissue comprises myocardial scar or infiltrate. In some embodiments, the target tissue comprises solid tumor tissue. In some embodiments, the target tissue is not tumor tissue. In some embodiments, the target tissue is not solid tumor tissue. In some embodiments, the target tissue comprises a neurologic tissue responsible for seizures.

In some embodiments, the induced protective and/or reparative cellular process comprises inflammation and/or a pro-fibrotic reaction, and the agent modulates inflammation and/or the pro-fibrotic reaction in the target tissue to be ablated. Accordingly, in one embodiment, the presently disclosed subject matter provides a method for augmenting ablation of a target tissue in a subject in need thereof, the method comprising: (a) administering to a subject in need thereof an effective amount of at least one agent that modulates inflammation and/or a pro-fibrotic reaction in a target tissue to be ablated in the subject; and (b) applying an ablative energy to the target tissue to be ablated in the subject, wherein the at least one agent modulates inflammation and/or the pro-fibrotic reaction in the target tissue to be ablated in the subject, thereby increasing the sensitization of the target tissue to the ablative energy, and augmenting ablation of the target tissue in the subject.

In some embodiments, the agent modulates inflammation in a target cardiac tissue to be ablated, thereby increasing the sensitization of the target cardiac tissue to the ablative energy, and augmenting ablation of the target cardiac tissue.

In some embodiments, the agent modulates a pro-fibrotic reaction in a target tissue cardiac tissue to be ablated, thereby increasing the sensitization of the target tissue cardiac tissue to the ablative energy, and augmenting ablation of the target cardiac tissue.

In some embodiments, the agent modulates inflammation and a pro-fibrotic reaction in a target cardiac tissue to be ablated, thereby increasing the sensitization of the target cardiac tissue to the ablative energy, and augmenting ablation of the target cardiac tissue.

Examples of agents that can be used to modulate inflammation (i.e., anti-inflammatory agent) and/or a pro-fibrotic reaction include, without limitation, steroids, non-steroidal anti-inflammatory drugs (NSAIDs), colchicine, and analogs or derivatives thereof.

As used herein, "anti-inflammatory agent" refers to an agent that may be used to prevent or reduce an inflammatory response or inflammation in a cell, tissue, organ, or subject. Exemplary anti-inflammatory agents contemplated for use include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus, prodrugs thereof, co-drugs thereof, and combinations thereof. The anti-inflammatory agent may also be a biological inhibitor of proinflammatory signaling molecules including antibodies to such biological inflammatory signaling molecules.

Examples of colchicine derivatives of use herein include, without limitation, the 4-modified colchicine compounds described in WO/2011/021397A1, the N-deacetylcolchicine and N-deacetylthiocolchicine derivatives described in U.S. Pat. No. 6,825,236, the colchicine neoglycosides described in U.S. Publication No. 2013/0012466, which are each incorporated herein by reference in their entirety.

In some embodiments, the agent that modulates the pro-fibrotic response comprises an antifibrotic agent. As used herein, "antifibrotic agent" refers to an agent that may be used to prevent or reduce a pro-fibrotic response in a cell, tissue, or organ. Exemplary anti-fibrotic agents contemplated for use include, without limitation, colchicine; inhibitors of molecular pathways involved in the fibrotic response, such as TGF-beta signaling inhibitors, including for example inhibitors of TGF-beta1, inhibitors of TGF-beta2, inhibitors of TGF-beta3; ALK inhibitors (e.g., SM305); inhibitors of a downstream target of c-Abl, such as inhibitors of profibrotic mediators selected from the group consisting of PKCgamma/Fli-1, Egr, and Smad1; inhibitors of connective tissue growth factor (CTGF/CCN2); inhibitors of platelet derived growth factor (PDGF), including inhibitors of PDGF-A, PDGF-B, and PDGF-C and PDGF-D; inhibitors of WNT-signaling; inhibitors of hedgehog signaling; inhibitors of notch signaling; inhibitors of endothelin-1; inhibition of homing of circulating profibrotic cells, such as inhibition of monocyte chemoattractant protein-1 (MCP-1/CCL-2); inhibition of Smads, including Smad3 (e.g., SIS3); tyrosine kinase inhibitors, such as dasatinib, nilotinib, nintedanib (BIBF 1120); Rho-associated kinase (ROCK) inhibitors (e.g., Y27632); hydroxymethylglutaryl-coenzyme A reductase inhibitors, such as statins; and combinations thereof. Additional anti-fibrotic agents and strategies for modulating pro-fibrotic responses can be found in Rosenbloom et al., "Biochimica et Biophysica Acta (BBA)—Molecular Basis of Disease. 2013; 1832(7):1088-1103, which is incorporated herein by reference in its entirety.

Examples of ablative energy that can be augmented by modulating inflammation and/or the pro-fibrotic reaction in a target tissue include, without limitation, thermally ablative energy, such as radiofrequency energy, microwave energy, ultrasound, and electromagnetic energy, and cryothermal ablative energy.

In some embodiments, the induced protective and/or reparative cellular process comprises a cold shock response process modulated by a cold shock protein (CSP), the agent decreases the expression level and/or activity of a cold shock protein in the target cardiac tissue to be ablated, and the ablative energy is a cryothermal energy.

Accordingly, in one embodiment, the presently disclosed subject matter provides a method for augmenting cryothermal ablation of a target cardiac tissue in a subject in need thereof, the method comprising: (a) administering to a subject in need thereof an effective amount of an agent that decreases the expression level and/or activity of a cold shock protein (CSP) in a target cardiac tissue to be ablated in the subject; and (b) applying a cryothermal energy to the target cardiac tissue to be ablated in the subject, wherein the agent decreases the expression level and/or activity of the cold shock protein in the target cardiac tissue to be ablated in the subject, thereby increasing the sensitization of the target cardiac tissue to the cryothermal energy, and augmenting cryothermal ablation of the target cardiac tissue in the subject.

Those skilled in the art will appreciate that the cellular response to sub-lethal thermal injury within the ablation periphery is complex and multifaceted. It is believed that cellular stress lead to up-regulation of oxidative pathways that induce apoptosis, and counterbalancing such stressors are reparative pathways that have cellular protective effects against apoptosis, especially the production of heat shock proteins in response to thermal injury.

In some embodiments, the induced protective and/or reparative cellular process comprises a heat shock response process modulated by a heat shock protein (HSP), the agent decreases the expression level and/or activity of a heat shock protein in the target cardiac tissue to be ablated, and the ablative energy is a thermal energy. Examples of suitable forms of thermal energy include, without limitation, radiofrequency energy, microwave energy, ultrasound, and electromagnetic energy.

As used herein, the terms "decrease," "reduce," or "inhibit," and grammatical derivations thereof, refers to the ability of an agent to block, partially block, interfere, decrease, reduce or deactivate a biological molecule, pathway or mechanism of action. Thus, one of ordinary skill in the art would appreciate that the term "inhibit" encompasses a complete and/or partial loss of activity, e.g., a loss in activity by at least 10%, in some embodiments, a loss in activity by at least 20%, 30%, 50%, 75%, 95%, 98%, and up to and including 100%.

Accordingly, in one embodiment, the presently disclosed subject matter provides a method for augmenting radiofrequency ablation of a target cardiac tissue in a subject in need thereof, the method comprising: (a) administering to a subject in need thereof an effective amount of an agent that decreases the expression level and/or activity of a heat shock protein (HSP) in a target cardiac tissue to be ablated in the subject; and (b) applying a radiofrequency energy to the target cardiac tissue to be ablated in the subject, wherein the agent decreases the expression level and/or activity of the heat shock protein in the target cardiac tissue to be ablated, thereby sensitizing the target cardiac tissue to the radiofrequency energy, and augmenting radiofrequency ablation of the target cardiac tissue in the subject.

The presently disclosed subject matter contemplates any agent that is capable of decreasing the expression level and/or activity of a heat shock protein in a target tissue to be thermally ablated. As used herein, the term "expression" encompasses the processes by which nucleic acids (e.g., DNA) are transcribed to produce RNA, and RNA transcripts are translated into polypeptides. Accordingly, decreasing the "expression level" of a protein comprises decreasing levels of transcription and translation, as well as decreasing levels of protein already present in a cell, e.g., tagging the protein for degradation (e.g., via ubiquitination).

The presently disclosed subject matter contemplates decreasing the expression level and/or activity of any heat shock protein that is induced in a target tissue in response to application of thermal ablative energy to the target tissue.

Exemplary heat shock proteins include, without limitation, heat shock protein 60 (Hsp60), heat shock protein 70 (Hsp70), and heat shock protein 90 (Hsp90).

In some embodiments, the agent decreases the expression level and/or activity of Hsp60 in a target tissue (e.g., cardiac tissue), thereby increasing the sensitivity of the target tissue to thermal ablative energy. The presently disclosed subject matter contemplates any agent described herein that is capable of decreasing the expression level and/or activity of Hsp60 in a target tissue to be thermally ablated. Exemplary agents that decrease the expression level and/or activity of Hsp70 (also referred to as Hsp70 inhibitors) include, without limitation, mizoribine, epolactaene, EC3016, epolactaene tertiary butyl ester (ETB), lucilactaene, N-Formyl-3,4-methylenedioxy-benzylidine-γ-butyrolactam, quercetin (3,3',4',5,7-pentahydroxyflavone), carboranylphenoxyacetanilide, gossypol, (+)-Avrainvillamide, and analogs or derivatives thereof.

In some embodiments, the agent decreases the expression level and/or activity of Hsp70 in a target tissue (e.g., cardiac tissue), thereby increasing the sensitivity of the target tissue to thermal ablative energy. Exemplary agents that decrease the expression level and/or activity of Hsp70 (also referred to as Hsp70 inhibitors) include, without limitation, the small molecule Hsp70 inhibitors described in WO/2015/130922, novel compounds of formula I and formula II or pharmaceutically acceptable salts thereof described in WO/2015/175707, DNA encoding proteins that inhibit Hsp70 function described in U.S. Publication No. 2003/0023071, each of which is incorporated herein by reference in its entirety.

In some embodiments, the agent decreases the expression level and/or activity of Hsp90 in a target tissue (e.g., cardiac tissue), thereby increasing the sensitivity of the target tissue to thermal ablative energy. Exemplary agents that decrease the expression level and/or activity of Hsp90 (also referred to herein as Hsp90 inhibitors) include, without limitation, 17-AAG (Tanespimycin); benzoquinone ansamycins, such as, geldanamycin and geldanamycin derivatives (e.g. 17-alkylamino-17-desmethoxy-geldanamycin ("17-AAG") and 17-(2 dimethylaminoethyl)amino-17-desmethoxy-geldanamycin ("17-DMAG")), 11-O-methyl-17-(2-(1-azetidinyl)ethyl)amino-17-demethoxygeldanamycin (A), 11-O-methyl-17-(2-dimethylaminoethyl)amino-17-demethoxygeldanamycin (B), and 11-O-methyl-17-(2-(1 pyrrolidinyl)ethyl)amino-17-demethoxygeldanamycin (C); 2-(4-(3-acetylcarnitineacyloxy)cyclohexylamino)-4-(1-(3,6, 6-trimethyl-4-oxy-4,5,6,7-tetrahydroindazole))benzamide, as described in U.S. Publication No. 2013/0190509; Luminespib (AUY-922, NVP-AUY922) and Ganetespib (STA-9090); radicicol; triazole derivatives of formula (1), and pharmacologically acceptable salts and prodrugs thereof described in U.S. Pat. No. 8,399,464, each of which is incorporated herein by reference in its entirety. Additional preferred geldanamycin derivatives are described in Santi et al., US 2003/0114450 A1 (2003). In some embodiments, the heat shock protein inhibitor is quercetin.

Those skilled in the art will appreciate that heat shock proteins can ameliorate apoptosis through a variety of mechanisms, including inhibition of procaspase 9 activation, prevention of cytochrome c release from mitochrondria, and JNK phosphorylation. Accordingly, it is believed that agents that inhibit procaspase 9 activation in a target tissue to be thermally ablated, agents that prevent cytochrome c release from mitochondria in a target tissue to be thermally ablated, and agents that modulate JNK phosphorylation in a target tissue to be thermally ablated, can be used to increase the sensitivity of the target tissue to thermal ablative energy, thereby augmenting thermal ablation of the target tissue.

In some embodiments, the method includes administering to the subject an effective amount of a toxin (e.g., a myocardial toxin), for example, by targeting the toxin to a target tissue to be ablated, for example, using a presently disclosed composition comprising metallic nanoparticles.

II. Augmenting Radiofrequency Ablation of Tissue Using Magnetically Guided Metallic Nanoparticles The presently disclosed subject relates to methods for augmenting radiofrequency ablation of target tissues (e.g., cardiac tissue) using magnetically guided nanoparticles. In some aspects, the presently disclosed subject matter provides a method for augmenting radiofrequency ablation of target cardiac tissue using metallic nanoparticles that are magnetically guided to a target cardiac tissue to be ablated. Work described in the examples herein demonstrates that ablation of cardiac tissue treated with metallic nanoparticles augments local radiofrequency heating, for example, by increasing ablation lesion size, providing a greater reduction in electrical impedance, and/or increased thermal conductivity in target cardiac tissue to be thermally ablated. Work described in the examples herein further demonstrates that metallic nanoparticles can be magnetically guided to a target cardiac tissue radiofrequency ablation site for precise targeting of myocardial tissues. It is believed that augmented radiofrequency ablation of target cardiac tissue using magnetically guided nanoparticles can be used to treat a variety of cardiac diseases (e.g., cardiac arrhythmias).

In an aspect, the presently disclosed subject matter provides a method for augmenting radiofrequency ablation of a target cardiac tissue in a subject in need thereof, the method comprising: (a) administering an effective amount of a composition comprising metallic nanoparticles to a subject; (b) using a magnetic field to guide the metallic nanoparticles to a target cardiac tissue to be ablated in the subject; and (c) applying a radiofrequency energy to the target cardiac tissue in the presence of the metallic nanoparticles guided to the target cardiac tissue, thereby augmenting radiofrequency ablation of the target cardiac tissue in the subject.

As used herein, the term "nanoparticle," refers to a particle having at least one dimension in the range of about 1 nm to about 1000 nm, including any integer value between 1 nm and 1000 nm (including about 1, 2, 5, 10, 20, 50, 60, 70, 80, 90, 100, 200, 500, and 1000 nm and all integers and fractional integers in between). In some embodiments, the nanoparticle has at least one dimension, e.g., a diameter, of about 100 nm. In some embodiments, the nanoparticle has a diameter of about 200 nm. In other embodiments, the nanoparticle has a diameter of about 500 nm. In yet other embodiments, the nanoparticle has a diameter of about 1000 nm (1 μm). In such embodiments, the particle also can be referred to as a "microparticle." Thus, the term "microparticle" includes particles having at least one dimension in the range of about one micrometer (μm), i.e., $1 \times 10^{-6}$ meters, to about 1000 μm. The term "particle" as used herein is meant to include nanoparticles and microparticles.

The presently disclosed subject matter contemplates the use of any metallic nanoparticle that is capable of being guided by a magnetic field and/or magnet to a target tissue when administered to a subject. Exemplary metallic nanoparticles of use herein include, without limitation, copper nanoparticles, gadolinium nanoparticles, gold nanoparticles, iron nanoparticles, titanium nanoparticles, and combinations thereof. In some embodiments, the nanoparticles can be coated. For example, the metallic nanoparticles (e.g., iron) can be coated with carbon, for example, to impart different paramagnetic properties.

The presently disclosed subject matter contemplates using a variety of differently shaped metallic nanoparticles. Exemplary such nanoparticles include, without limitation, coral-shaped, cube-shaped, rod-shaped, spherical-shaped nanoparticles, tetrapod-shaped, triangular-shaped, and combinations thereof.

In some embodiments, the metallic nanoparticles are not carbon nanotubes.

The presently disclosed subject matter contemplates delivering the metallic nanoparticles in any suitable delivery vehicle alone, or optionally together with at least one additional presently disclosed agent (e.g., at least one agent that modulates a protective and/or reparative cellular process induced in a target tissue by application of an ablative energy to the target tissue). In some embodiments, the delivery vehicle comprises liposomes. In some embodiments, the composition comprises liposomes. In some embodiments, the composition is encapsulated in liposomes. In some embodiments, the liposomes are temperature-sensitive liposomes. In some embodiments, the liposomes are heat-sensitive liposomes. In some embodiments, the temperature-sensitive liposomes (e.g., heat-sensitive) release their contents at a range of between about 40 degrees Celsius and about 50 degrees Celsius.

In some embodiments, the metallic nanoparticles are encapsulated in liposomes. In some embodiments, the metallic nanoparticles are encapsulated in temperature-sensitive liposomes. In some embodiments, the metallic nanoparticles are encapsulated in heat-sensitive liposomes.

It is to be understood that the any agent described herein can be included in the composition comprising magnetic nanoparticles. In some embodiments, the composition further comprises at least one agent that modulates a protective and/or reparative cellular process induced in a target tissue by application of an ablative energy to the target tissue. In some embodiments, at least one agent that modulates a protective and/or reparative cellular process induced in a target tissue by application of an ablative energy to the target tissue is encapsulated in liposomes (e.g., temperature sensitive liposomes, e.g., heat-sensitive liposomes). In some embodiments, the composition further comprises an agent that decreases the expression level and/or activity of a heat shock protein described herein. In some embodiments, the composition further comprises at least one agent that induces apoptosis. In some embodiments, the composition further comprises sonosensitizers. In some embodiments, the composition further comprises polynucleotides (e.g., anti-sense, ribozymes, siRNA). In some embodiments, the composition further comprises polypeptides (e.g., enzymes and antibodies). In some embodiments, the composition further comprises agents that bind (e.g., oligomerize or complex) with a Bcl-2 family protein such as Bax. In some embodiments, the composition further comprises alkaloids. In some embodiments, the composition further comprises alkylating agents. In some embodiments, the composition further comprises antibiotics. In some embodiments, the composition further comprises antimetabolites. In some embodiments, the composition further comprises hormones. In some embodiments, the composition further comprises platinum compounds. In some embodiments, the composition further comprises monoclonal or polyclonal antibodies (e.g., antibodies conjugated with anticancer drugs, toxins, defensins). In some embodiments, the composition further comprises toxins (e.g., cardiac specific toxins, e.g., myocardial toxins, such as ethanol, botulinum toxin, and tetrodotoxin (TTX). In some embodiments, the composition further comprises radionuclides. In some embodiments, the composition further comprises biological response modifiers (e.g., interferons (e.g., IFN-a) and interleukins (e.g., IL-2)). In some embodiments, the composition further comprises adoptive immunotherapy agents. In some embodiments, the composition further comprises hematopoietic growth factors. In some embodiments, the composition further comprises agents that induce cell differentiation (e.g., all-trans-retinoic acid). In some embodiments, the composition further comprises gene therapy reagents (e.g., antisense therapy reagents and nucleotides). In some embodiments, the composition further comprises angiogenesis inhibitors. In some embodiments, the composition further comprises proteosome inhibitors. In some embodiments, the composition further comprises NF-KB modulators. In some embodiments, the composition further comprises anti-CDK compounds. In some embodiments, the composition further comprises HDAC inhibitors. In some embodiments, the composition further comprises heavy metals (e.g., barium, gold, or platinum). In some embodiments, the composition further comprises chemotherapeutic agents (e.g., doxorubicin or cisplatin) and the like.

In some embodiments, the metallic nanoparticles are encapsulated in liposomes together with at least one agent that modulates a protective and/or reparative cellular process induced in a target tissue by application of an ablative energy to the target tissue.

In some embodiments, the agent that modulates a protective and/or reparative cellular process induced in a target tissue by application of an ablative energy to the target tissue is quercetin, or an analog or derivative thereof. In some embodiments, the agent that decreases the expression level and/or activity of a heat shock protein is quercetin, or an analog or derivative thereof. Exemplary quercetin analogs or derivatives of use herein include, without limitation, the quercetin compounds (e.g., zinc complex, selenium complex, fluorinated compound, glycosidic compound, pentaacetylquercetin compound, and trimethylquercetin compound) described in WO/1992/013851, the semi-synthetic derivatives of quercetin formula I and pharmaceutically acceptable salts, hydrates and solvates described in WO/2013/130020, novel quercetin derivatives of formula (I) and pharmaceutically acceptable salts, hydrates, and solvates thereof described in U.S. Publication no. 2011/0034413, quercetin glucuronide as described in U.S. Pat. No. 8,795,956, which are each incorporated herein by reference in their entirety.

In some embodiments, the agent that modulates a protective and/or reparative cellular process induced in a target tissue by application of an ablative energy to the target tissue is 17-allyl amino geldanamycin (17-AAG), or an analog, derivative, or pro-drug thereof. In some embodiments, the agent that decreases the expression level and/or activity of a heat shock protein is 17-AAG, or an analog, derivative thereof, or pro-drug thereof. Exemplary pro-drugs of 17-AAG are described in U.S. Publication No. 2006/025270, which is incorporated herein by reference in its entirety. Exemplary analogs or derivatives of 17-AAG include, without limitation, In some embodiments, the agent that modulates a protective and/or reparative cellular process induced in a target tissue by application of an ablative energy to the target tissue is celestrol, or an analog or derivative thereof. In some embodiments, the agent that decreases the expression level and/or activity of a heat shock protein is celestrol, or an analog or derivative thereof.

In some embodiments, the metallic nanoparticles are functionalized with at least one additional agent (e.g., an agent disclosed herein), optionally via a linker. For example, the metallic nanoparticles can be functionalized with at least one agent that modulates a protective and/or reparative cellular process induced in a target tissue by application of an ablative energy to the target tissue. In some embodiments, the metallic nanoparticles are functionalized with at least one agent that decreases the expression level and/or activity of a heat shock protein via a thermally labile linking group that disintegrates or breaks and releases the at least one agent. In this way, the metallic nanoparticles can be magnetically guided to a target tissue (e.g., cardiac tissue) and upon application of a thermally ablative energy (e.g., radiofrequency energy), the thermally labile linking group breaks and locally releases the at least one agent (e.g., that decreases the expression level and/or activity of a heat shock protein) in the target tissue to be ablated, thereby augmenting ablation of the target tissue while locally administering the at least one agent to the target tissue.

The presently disclosed subject matter contemplates additional agents for use in the compositions and methods, including, but are not limited to, agents that induce apoptosis; sonosensitizers; polynucleotides (e.g., anti-sense, ribozymes, siRNA); polypeptides (e.g., enzymes and antibodies); agents that bind (e.g., oligomerize or complex) with a Bcl-2 family protein such as Bax; alkaloids; alkylating agents; antibiotics; antimetabolites; hormones; platinum compounds; monoclonal or polyclonal antibodies (e.g., antibodies conjugated with anticancer drugs, toxins, defensins), toxins (e.g., cardiac specific toxins, e.g., myocardial toxins, such as ethanol, botulinum toxin, and tetrodotoxin (TTX); radionuclides; biological response modifiers (e.g., interferons (e.g., IFN-α) and interleukins (e.g., IL-2)); adoptive immunotherapy agents; hematopoietic growth factors; agents that induce cell differentiation (e.g., all-trans-retinoic acid); gene therapy reagents (e.g., antisense therapy reagents and nucleotides); angiogenesis inhibitors; proteosome inhibitors: NF-KB modulators; anti-CDK compounds; HDAC inhibitors; heavy metals (e.g., barium, gold, or platinum); chemotherapeutic agents (e.g., doxorubicin or cisplatin) and the like. Numerous other examples of toxic compounds are known to those skilled in the art.

In some embodiments, toxic agents are sonosensitizers. Examples of sonosensitizers include, but are not limited to, porphyrins (e.g., hematoporphyrin, diacetlyhematoporphyn-mitomycin-C conjugate, photofrin II, mesoporphyrin, protoporphyrin IX, copper protoporphyrin, tetraphenylporphine tetrasulfonate, ATX-70, ATX-S10, pheophorbide-a, ClAl-phtalocyanine tetrasulfonate, and chlorine PAD-S31), tenoxicam, piroxicam, rose bengal, erythrosine B, merocyanine 540, dimethylformamide, cytosine arabinoside, pyridoxarbazole, 2,2'-azobis(2-amdinopropane), 5,5'-dimethyl-1-pyrroline-X-oxide, e-pyridyl-1-oxide-N-t-butylnitrone, and anti-cancer agents (e.g., nitrogen mustard, cyclophosmadmide, bleomycin, adriamycin, FAD 104, amphotericin B, mitomycin C, daunomycin, cisplatin, etoposide, diaziquone, dihydroxy(oxbi-guoanido) boron, and 5-fluorouracil) (See e.g., Rosenthal et al, Ultrasonics Sonochemistry 11 (2004) 349; herein incorporated by reference in its entirety).

In some embodiments, toxic agents comprise agents that induce or stimulate apoptosis. Agents that induce apoptosis include, but are not limited to, radiation (e.g., X-rays, gamma rays, UV); tumor-derived growth factor ligands, receptors, and analogs; kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like. Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycoformycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

The presently disclosed subject matter contemplates the use of any magnetic field that is capable of exhibiting a sufficient pound pull force to guide the magnetic particles to a target tissue to be ablated. In some embodiments, the magnetic field is generated by a magnet that exhibits a pound pull force of between 0.001 and 1000. Those skilled in the art will appreciate that the pound pull force of any particular magnet used may vary depending on several factors, for example, based on the distance and placement of the magnet relative to the magnetic nanoparticles and target tissue. In some embodiments, the magnet has a pound pull force of about 310.

In some embodiments, the magnet is placed adjacent to the target cardiac tissue to be ablated. For example, to guide a composition comprising metallic nanoparticles administered to a subject to a target cardiac tissue, a magnet can be placed outside of the body in proximity to the chest cavity of the subject, to attract the composition comprising metallic nanoparticles to the target cardiac tissue in the subject. In some embodiments, the magnet is placed adjacent to the tip of a mapping catheter that is not used to ablate the target tissue. In some embodiments, the magnet is placed within the tip of a mapping catheter that is not used to ablate the target tissue. In some embodiments, the magnet is incorporated into an ultrasound catheter (e.g., near the catheter tip).

In some embodiments, the magnet comprises a component of a stand-alone magnetic catheter. In some embodiments, the magnet comprises a magnet incorporated into a tip of an ablation catheter. In some embodiments, the magnet comprises an electromagnet. In some embodiments, the electromagnet is capable of turning on and off. In some embodiments, the magnet comprises an electromagnet in a radiofrequency energy catheter wherein the electromagnet is located in the same tip that emits the radiofrequency energy.

In some embodiments, the magnet is a rare-earth magnet. In some embodiments, the magnet is a neodymium magnet.

The presently disclosed subject matter contemplates the use of any source or radiofrequency energy. In some embodiments, the radiofrequency energy is applied using an ablation catheter. In some embodiments, the ablation catheter comprises a force-sensing irrigated tip radiofrequency catheter (e.g., SmartTouch Thermocool, Biosense-Webster, Diamond Bar, Calif.). In some embodiments, the ablation catheter comprises a non-irrigated radiofrequency ablation catheter (Biosense-Webster, Diamond Bar, Calif.). In some embodiments, the ablation catheter comprises a magnetic tip. In some embodiments, the ablation catheter comprises a tip comprising an electromagnet and a radiofrequency energy source. In some embodiments, the magnetic tip of the ablation catheter is used to guide the metallic nanoparticles to the target tissue (e.g., cardiac tissue) to be ablated. In some embodiments, a separate mapping catheter or ultrasound catheter has a magnetic tip that is used to guide the metallic nanoparticles to the target tissue (e.g., cardiac tissue) to be ablated.

Those skilled in the art will appreciate that the amount of radiofrequency energy applied in any particular situation may vary depending on a number of factors, including the target tissue to be ablated. In some embodiments, the radiofrequency energy applied is between 1 W and 100 W. In some embodiments, the radiofrequency energy applied is between 10 W and 50 W.

The terms "subject" and "patient" are used interchangeably herein. The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease.

In some embodiments, the subject is selected for treatment of a cardiac arrhythmia. In some embodiments, the cardiac arrhythmia is selected from the group consisting of atrial fibrillation, premature atrial contractions, wandering atrial pacemaker, multifocal atrial tachycardia, atrial flutter, supraventricular tachycardia, tachycardia selected from the group consisting of atrial tachycardia, atrioventricular nodal reentrant tachycardia, and atrioventricular reciprocating tachycardia, junctional rhythm, junctional tachycardia, premature junctional contraction, premature ventricular contractions, accelerated idioventricular rhythm, monomorphic ventricular tachycardia, polymorphic ventricular tachycardia, ventricular fibrillation, heart blocks, long QT syndrome, Brugada syndrome, catecholaminergic polymorphic ventricular tachycardia, arrhythmogenic right ventricular dysplasia, dilated cardiomyopathy, cardiomyopathy due to prior myocardial infarction, and abnormal Purkinje potentials leading to ventricular arrhythmias including electrical storms; and combinations thereof. In some embodiments, the subject has a pacemaker. In some embodiments, the subject has an implantable cardiac defribllator.

The presently disclosed subject matter contemplates imaging target tissue to be ablated. In some embodiments, the presently disclosed methods include imaging the metallic nanoparticles in the subject. In some embodiments, the presently disclosed compositions comprise an imaging agent. The presently disclosed subject matter contemplates the use of any imaging agent available to the skilled artisan. In some embodiments, the imaging agent is encapsulated in a liposome (e.g., temperature-sensitive liposome, e.g., heat-sensitive liposome) together with or separately from the metallic nanoparticles. In some embodiments, the imaging agent is functionalized to the metallic nanoparticles, optionally via a linker moiety. In some embodiments, the metallic nanoparticle serves as an imaging agent. In some embodiments, the imaging agent is a magnetic material (e.g., iron for MRI). In some embodiments, the imaging agent is a protein that catalyzes a luminescent reaction (e.g., luciferins such as luciferase for bioluminescent imaging). In some embodiments, the imaging agent is a fluorescent dye (e.g., rodamine or fluorescein isothiocyanate for fluorescent imaging). In some embodiments, the imaging agent is a fluorescent protein (e.g., green fluorescent protein, red fluorescent protein, etc.). In some embodiments, the imaging agent is a radioactive element (e.g., for autoradiography). In some embodiments, the imaging agent comprises a nanomaterial to be used as a contrast agent for X-ray, CT, MRI, PET, and combinations thereof. Exemplary contrast agents include, without limitation, gadolium contrast agents, fluorescent agents (e.g., Alizarin Red S), and contrast agents described in U.S. Pat. Nos. 7,412,279 and 6,540,981, both of which are herein incorporated by reference in their entirety.

The presently disclosed subject matter contemplates administering an effective amount of at least one prophylactic agent to a subject to reduce the risk and/or severity of an adverse reaction to a composition administered to the subject. For example, at least one prophylactic agent can be administered (e.g., intravenously) to the subject to reduce the risk and/or severity of an adverse reaction to a presently disclosed liposome (e.g., prior to liposomal infusion of iron nanoparticles).

In some embodiments, the at least one prophylactic agent comprises an antianaphylactic agent, for example, to prevent or reduce the likelihood and/or severity of an anaphylactic reaction in the subject. In some embodiments, the at least one antianaphylactic agent is dexamethasone.

In some embodiments, the at least one prophylactic agent comprises an antihypotensive agent, for example, to prevent or reduce the likelihood and/or severity of the subject developing hypotension. In some embodiments, the antihypotensive agent is epinephrenine.

III. Methods of Treatment

The presently disclosed subject matter contemplates treating any condition, disease, or disorder in which augmented ablation of a target tissue in accordance with the agents, compositions, and methods disclosed herein would be desirable.

In an aspect, a method for treating a subject in need of augmented ablation of target tissue comprises: (a) performing a presently disclosed method for augmenting ablation of a target tissue in the subject; and (b) applying an ablative energy to the target tissue in the subject, thereby treating the subject in need of augmented ablation of the target tissue.

In some embodiments, augmenting ablation comprises administering to the subject an effective amount of an agent that modulates a protective and/or reparative cellular process induced in the target tissue by application of the ablative energy to the target tissue, thereby sensitizing the target tissue to the ablative energy, and augmenting ablation of the target tissue in the subject.

In some embodiments, augmenting ablation comprises administering to the subject an effective amount of a composition comprising metallic nanoparticles, and using a magnetic field to guide the metallic nanoparticles to the target tissue to be ablated, thereby augmenting ablation of the target tissue in the subject.

In an aspect, the presently disclosed subject matter provides a method for treating a cardiac arrhythmia in a subject in need thereof, the method comprising: (a) performing a presently disclosed method for augmenting ablation of a target cardiac tissue in the subject; and (b) applying an ablative energy to the target cardiac tissue in the subject, thereby treating the cardiac arrhythmia in the subject.

In some embodiments, augmenting ablation comprises administering to the subject an effective amount of an agent that modulates a protective and/or reparative cellular process induced in the target cardiac tissue by application of the ablative energy to the target cardiac tissue, thereby sensitizing the target cardiac tissue to the ablative energy, and augmenting ablation of the target tissue in the subject. In some embodiments, the induced protective and/or reparative cellular process comprises a cold shock response process modulated by a cold shock protein (CSP), the agent decreases the level and/or activity of a cold shock protein in the target tissue, and the ablative energy is a cryothermal energy. In some embodiments, the induced protective and/or reparative cellular process comprises a heat shock response process modulated by a heat shock protein (HSP), the agent decreases the level and/or activity of a heat shock protein in the target tissue, and the ablative energy is a thermal energy, wherein the thermal energy is optionally selected from the group consisting of radiofrequency energy, microwave energy, ultrasound, electromagnetic energy.

In some embodiments, augmenting ablation comprises administering to the subject an effective amount of a composition comprising metallic nanoparticles, and using a magnetic field to guide the metallic nanoparticles to the target cardiac tissue to be ablated, thereby augmenting ablation of the target cardiac tissue in the subject. In such embodiments, the ablative energy comprises a radiofrequency energy applied the target cardiac tissue in the presence of the metallic nanoparticles guided to the target cardiac tissue.

In some embodiments, augmenting ablation comprises: (i) administering to the subject an effective amount of an agent that modulates a protective and/or reparative cellular process induced in the target cardiac tissue by application of the ablative energy to the target cardiac tissue, thereby sensitizing the target cardiac tissue to the ablative energy, and (ii) administering to the subject an effective amount of a composition comprising metallic nanoparticles, and using a magnetic field to guide the metallic nanoparticles to the target cardiac tissue to be ablated, thereby augmenting ablation of the target cardiac tissue in the subject.

In some embodiments, augmenting ablation comprises administering to the subject an effective amount of a composition comprising metallic nanoparticles and at least one agent that modulates a protective and/or reparative cellular process induced in the target cardiac tissue by application of the ablative energy to the target cardiac tissue, and using a magnetic field to guide the composition comprising the metallic nanoparticles and at least one agent that modulates a protective and/or reparative cellular process induced in the target cardiac tissue by application of the ablative energy to the target cardiac tissue to the target cardiac tissue to be ablated, thereby augmenting ablation of the target cardiac tissue in the subject.

Generally, the presently disclosed compositions (e.g., comprising metallic nanoparticles and/or at least one agent that modulates a protective and/or reparative cellular process induced in a target tissue by application of an ablative energy to the target tissue) can be administered to a subject for therapy by any suitable route of administration, including orally, nasally, transmucosally, ocularly, rectally, intravaginally, or parenterally, including intravenous, intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections, intracisternally, topically, as by powders, ointments or drops (including eyedrops), including buccally and sublingually, transdermally, through an inhalation spray, or other modes of delivery known in the art.

The phrases "systemic administration", "administered systemically", "peripheral administration" and "administered peripherally" as used herein mean the administration of compositions such that they enter the patient's system and, thus, are subject to metabolism and other like processes, for example, subcutaneous or intravenous administration.

The phrases "parenteral administration" and "administered parenterally" as used herein mean modes of administration other than enteral and topical administration, usually by injection, and includes, without limitation, intravenous, intramuscular, intarterial, intrathecal, intracapsular, intraorbital, intraocular, intracardiac, intradermal, intraperitoneal, transtracheal, subcutaneous, subcuticular, intraarticular, subcapsular, subarachnoid, intraspinal and intrasternal injection and infusion.

The presently disclosed pharmaceutical compositions can be manufactured in a manner known in the art, e.g. by means of conventional mixing, dissolving, granulating, dragee-making, levitating, emulsifying, encapsulating, entrapping or lyophilizing processes.

In another embodiment, the presently disclosed pharmaceutical compositions may comprise PEGylated therapeutics (e.g., PEGylated antibodies). PEGylation is a well-established and validated approach for the modification of a range of antibodies, proteins, and peptides and involves the attachment of polyethylene glycol (PEG) at specific sites of the antibodies, proteins, and peptides (Chapman (2002) *Adv. Drug Deliv. Rev.* 54:531-545). Some effects of PEGylation include: (a) markedly improved circulating half-lives in vivo due to either evasion of renal clearance as a result of the polymer increasing the apparent size of the molecule to above the glomerular filtration limit, and/or through evasion of cellular clearance mechanisms; (b) improved pharmacokinetics; (c) improved solubility—PEG has been found to be soluble in many different solvents, ranging from water to many organic solvents such as toluene, methylene chloride, ethanol and acetone; (d) PEGylated antibody fragments can be concentrated to 200 mg/ml, and the ability to do so opens up formulation and dosing options such as subcutaneous administration of a high protein dose; this is in contrast to many other therapeutic antibodies which are typically administered intravenously; (e) enhanced proteolytic resistance of the conjugated protein (Cunningham-Rundles et. al. (1992) *J. Immunol. Meth.* 152:177-190); (f) improved bioavailability via reduced losses at subcutaneous injection sites; (g) reduced toxicity has been observed; for agents where toxicity is related to peak plasma level, a flatter pharmacokinetic profile achieved by subcutaneous administration of PEGylated protein is advantageous; proteins that elicit an immune response which has toxicity consequences may also benefit as a result of PEGylation; and (h) improved thermal and mechanical stability of the PEGylated molecule.

Pharmaceutical compositions for parenteral administration include aqueous solutions of compositions. For injection, the presently disclosed pharmaceutical compositions can be formulated in aqueous solutions, for example, in some embodiments, in physiologically compatible buffers, such as Hank's solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of compositions include fatty oils, such as sesame oil, or synthetic fatty acid esters, such as ethyl oleate or triglycerides, or liposomes. Optionally, the suspension also can contain suitable stabilizers or agents that increase the solubility of the compositions to allow for the preparation of highly concentrated solutions.

For nasal or transmucosal administration generally, penetrants appropriate to the particular barrier to be permeated are used in the formulation. Such penetrants are generally known in the art.

For inhalation delivery, the agents of the disclosure also can be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Additional ingredients can be added to compositions for topical administration, as long as such ingredients are pharmaceutically acceptable and not deleterious to the epithelial cells or their function. Further, such additional ingredients should not adversely affect the epithelial penetration efficiency of the composition, and should not cause deterioration in the stability of the composition. For example, fragrances, opacifiers, antioxidants, gelling agents, stabilizers, surfactants, emollients, coloring agents, preservatives, buffering agents, and the like can be present. The pH of the presently disclosed topical composition can be adjusted to a physiologically acceptable range of from about 6.0 to about 9.0 by adding buffering agents thereto such that the composition is physiologically compatible with a subject's skin.

Regardless of the route of administration selected, the presently disclosed compositions are formulated into pharmaceutically acceptable dosage forms such as described herein or by other conventional methods known to those of skill in the art.

In general, the "effective amount" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In some embodiments of the presently disclosed subject matter, the active agents are combined and administered in a single dosage form. In some embodiments, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of two (or more) agents can be varied so long as the beneficial effects of the combination of these agents are achieved. Accordingly, the phrase "in combination with" refers to the administration of a presently disclosed composition and, optionally, additional agents either simultaneously, sequentially, or a combination thereof. Therefore, a subject administered a combination of a presently disclosed composition and, optionally, additional agents can receive a presently disclosed composition and, optionally, additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising either a presently disclosed composition and, optionally, additional agents, or they can be administered to a subject as a single pharmaceutical composition comprising all agents. In some embodiments, one agent is administered and the other agent is administered three days later. In some embodiments, one agent is administered and the other agent is administered 4, 5, 6, 7, 8, 9, 10, 15, 20 days or more later.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index(SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another aspect, the presently disclosed subject matter provides a pharmaceutical composition and optionally, additional agents, alone or in combination with one or more additional therapeutic agents in admixture with a pharmaceutically acceptable excipient.

More particularly, the presently disclosed subject matter provides a pharmaceutical composition and, optionally, additional agents and a pharmaceutically acceptable carrier.

In therapeutic and/or diagnostic applications, the agents of the disclosure can be formulated for a variety of modes of administration, including systemic and topical or localized administration. Techniques and formulations generally may be found in Remington: The Science and Practice of Pharmacy ($20^{th}$ ed.) Lippincott, Williams and Wilkins (2000).

Use of pharmaceutically acceptable inert carriers to formulate the agents herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the agents according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

IV. Compositions

The presently disclosed subject matter contemplates compositions comprising the presently disclosed metallic nanoparticles and/or presently disclosed agents that modulate a protective and/or reparative cellular process induced in a target tissue by application of an ablative energy to the target tissue. In some embodiments, the induced protective and/or reparative cellular process comprises a cold shock response process modulated by a cold shock protein (CSP), and the agent decreases the level and/or activity of a cold shock protein in the target tissue to be ablated. In some embodiments, the induced protective and/or reparative cellular process comprises a heat shock response process modulated by a heat shock protein (HSP), and the agent decreases the level and/or activity of a heat shock protein in the target tissue to be ablated.

In some embodiments, the composition comprises temperature-sensitive liposomes, the metallic nanoparticles and/or the at least one agent are encapsulated in the temperature-sensitive liposomes, and the temperature-sensitive liposomes release the metallic nanoparticles and at least one agent in the target tissue to be ablated upon exposure to a threshold temperature. In some embodiments, the threshold temperature is between about 40 degrees Celsius and about 50 degrees Celsius.

In some embodiment, the composition comprises an agent that decreases the expression level and/or activity of hsp60. In some embodiment, the composition comprises an agent that decreases the expression level and/or activity of hsp70. In some embodiment, the composition comprises an agent that decreases the expression level and/or activity of hsp90. In some embodiments, the composition comprises quercetin or an analog or derivative thereof. In some embodiments, the composition comprises 17-AAG or an analog or derivative thereof. In some embodiments, the composition comprises celestrol or an analog or derivative thereof.

In some embodiments, the composition comprises an agent that inhibits procaspase 9 activation. In some embodiments, the composition comprises an agent that prevents cytochrome c release from mitochondria. In some embodiments, the composition comprises an agent that modulates JNK phosphorylation.

In some embodiments, the composition comprises at least one prophylactic agent. In some embodiments, the composition comprises an antianaphylactic agent. In some embodiments, the composition comprises dexamethasone. In some embodiments, the composition comprises an antihypotensive agent. In some embodiments, the composition comprises epinepherenine.

In some embodiments, the composition comprises at least one antiarrhythmic agent. Exemplary antiarrhythmic agents of use herein include, without limitation, amiodarone, bepridil hydrochloride, disopyramide, dofetilide, dronedarone, flecainide, ibutilidie, lidocaine, procainamide, propafenone, propranolol, quinidine, sotalol, tocainide, and combinations thereof.

In some embodiments, the composition comprises at least one calcium channel blocker. Exemplary calcium channel blockers of use herein include, without limitation, amlodipine, diltiazem, felodipine, isradipine, nicardipine, nifedipine, nimodipine, nisoldipine, verapamil, and combinations thereof.

In some embodiments, the composition comprises at least one beta-blocker. Exemplary beta-blockers of use herein include, without limitation, acebutolol, atenolol, betaxolol, bisoprolol/hydrochlorothiazide, carteolol, esmolol, metoprolol, nadolol, penbutolol, pindolol, propranolol, timolol, and combinations thereof.

In some embodiments, the composition comprises at least one anticoagulant. Exemplary anticoagulants of use herein include, without limitation, warfarin and aspirin.

In some embodiments, the composition comprises at least one agent that induces apoptosis. In some embodiments, the composition comprises sonosensitizers. In some embodiments, the composition comprises polynucleotides (e.g., anti-sense, ribozymes, siRNA). In some embodiments, the composition comprises polypeptides (e.g., enzymes and antibodies). In some embodiments, the composition comprises agents that bind (e.g., oligomerize or complex) with a Bcl-2 family protein such as Bax. In some embodiments, the composition comprises alkaloids. In some embodiments, the composition comprises alkylating agents. In some embodiments, the composition comprises antibiotics. In some embodiments, the composition comprises antimetabolites. In some embodiments, the composition comprises hormones. In some embodiments, the composition comprises platinum compounds. In some embodiments, the composition comprises monoclonal or polyclonal antibodies (e.g., antibodies conjugated with anticancer drugs, toxins, defensins). In some embodiments, the composition comprises toxins (e.g., cardiac specific toxins, e.g., myocardial toxins, such as ethanol, botulinum toxin, and tetrodotoxin (TTX). In some embodiments, the composition comprises radionuclides. In some embodiments, the composition comprises biological response modifiers (e.g., interferons (e.g., IFN-a) and interleukins (e.g., IL-2)). In some embodiments, the composition comprises adoptive immunotherapy agents. In some embodiments, the composition comprises hematopoietic growth factors. In some embodiments, the composition comprises agents that induce cell differentiation (e.g., all-trans-retinoic acid). In some embodiments, the composition comprises gene therapy reagents (e.g., antisense therapy reagents and nucleotides). In some embodiments, the composition comprises angiogenesis inhibitors. In some embodiments, the composition comprises proteosome inhibitors. In some embodiments, the composition comprises NF-KB modulators. In some embodiments, the composition comprises anti-CDK compounds. In some embodiments, the composition comprises HDAC inhibitors. In some embodiments, the composition comprises heavy metals (e.g., barium, gold, or platinum). In some embodiments, the composition comprises chemotherapeutic agents (e.g., doxorubicin or cisplatin) and the like.

V. Kits

In general, a presently disclosed kit contains some or all of the components, reagents, supplies, and the like to practice a method according to the presently disclosed subject matter. In some embodiments, the term "kit" refers to any intended article of manufacture (e.g., a package or a container) comprising a presently disclosed metallic nanoparticle and/or at least one agent that modulates a protective and/or reparative cellular process induced in a target tissue by application of an ablative energy to the target tissue (e.g., an agent that decreases the expression level and/or activity of at least one heat shock protein).

In some embodiments, the kit comprises a presently disclosed metallic nanoparticle and/or at least one agent that modulates a protective and/or reparative cellular process induced in a target tissue by application of an ablative energy to the target tissue (e.g., an agent that decreases the expression level and/or activity of at least one heat shock protein), and a set of particular instructions for augmenting ablation of a target tissue in a subject in need thereof, and/or treating a disease or disorder in a patient (e.g., cardiac arrhythmia). In some embodiments, the kit comprises a composition disclosed herein.

In some embodiment, the kit comprises an agent that decreases the expression level and/or activity of hsp60. In some embodiment, the kit comprises an agent that decreases the expression level and/or activity of hsp70. In some embodiment, the kit comprises an agent that decreases the expression level and/or activity of hsp90. In some embodiments, the kit comprises quecertin.

In some embodiments, the kit comprises an agent that inhibits procaspase 9 activation. In some embodiments, the kit comprises an agent that prevents cytochrome c release from mitochondria. In some embodiments, the kit comprises an agent that modulates JNK phosphorylation.

In some embodiments, the kit comprises at least one prophylactic agent. In some embodiments, the kit comprises an antianaphylactic agent. In some embodiments, the kit comprises dexamethasone. In some embodiments, the kit comprises an antihypotensive agent. In some embodiments, the kit comprises epinepherenine.

In some embodiments, the kit comprises at least one antiarrhythmic agent. In some embodiments, the kit comprises at least one calcium channel blocker. In some embodiments, the kit comprises at least one beta-blocker. In some embodiments, the kit comprises at least one anticoagulant.

In some embodiments, the kit comprises at least one agent that induces apoptosis. In some embodiments, the kit comprises sonosensitizers. In some embodiments, the kit comprises polynucleotides (e.g., anti-sense, ribozymes, siRNA). In some embodiments, the kit comprises polypeptides (e.g., enzymes and antibodies). In some embodiments, the kit comprises agents that bind (e.g., oligomerize or complex) with a Bcl-2 family protein such as Bax. In some embodiments, the kit comprises alkaloids. In some embodiments, the kit comprises alkylating agents. In some embodiments, the kit comprises antibiotics. In some embodiments, the kit comprises antimetabolites. In some embodiments, the kit comprises hormones. In some embodiments, the kit comprises platinum compounds. In some embodiments, the kit comprises monoclonal or polyclonal antibodies (e.g., antibodies conjugated with anticancer drugs, toxins, defensins). In some embodiments, the kit comprises toxins (e.g., cardiac specific toxins, e.g., myocardial toxins, such as ethanol, botulinum toxin, and tetrodotoxin (TTX). In some embodiments, the kit comprises radionuclides. In some embodiments, the kit comprises biological response modifiers (e.g., interferons (e.g., IFN-a) and interleukins (e.g., IL-2)). In some embodiments, the kit comprises adoptive immunotherapy agents. In some embodiments, the kit comprises hematopoietic growth factors. In some embodiments, the kit comprises agents that induce cell differentiation (e.g., all-trans-retinoic acid). In some embodiments, the kit comprises gene therapy reagents (e.g., antisense therapy reagents and nucleotides). In some embodiments, the kit comprises angiogenesis inhibitors. In some embodiments, the kit comprises proteosome inhibitors. In some embodiments, the kit comprises NF-KB modulators. In some embodiments, the kit comprises anti-CDK compounds. In some embodiments, the kit comprises HDAC inhibitors. In some embodiments, the kit comprises heavy metals (e.g., barium, gold, or platinum). In some embodiments, the kit comprises chemotherapeutic agents (e.g., doxorubicin or cisplatin) and the like.

The kit can be packaged in a divided or undivided container, such as a carton, bottle, ampule, tube, etc. The presently disclosed compositions can be packaged in dried, lyophilized, or liquid form. Additional components provided can include vehicles for reconstitution of dried components. Preferably all such vehicles are sterile and apyrogenic so that they are suitable for injection into a patient without causing adverse reactions.

VI. Certain Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

For the purposes of this specification and appended claims, unless otherwise indicated, the following abbreviations shall mean as follows: "NP" is nanoparticle; "RF" is radiofrequency; "FeO" is iron oxide; "MRI" is magnetic resonance imaging; "Ti" is titanium; "Cu" is copper; and "NS" is normal saline.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Enhanced Radiofrequency Ablation with Magnetically Directed Metallic Nanoparticles
Introduction Remote heating of metal placed near a source of radiofrequency (RF) energy within the heart has been previously described (Nguyen et al., 2015; Burke et al., 2001). This phenomenon has led to some safety concerns for patients undergoing cardiac MRI and for those undergoing catheter ablation (Bassen et al., 2006; Lakkireddy et al., 2005). However, application of this phenomenon for the purpose of improving cardiac ablation efficacy has not been previously explored.

We have previously demonstrated that a commonly used metal, gadolinium, can facilitate ablation of cardiac tissues (Nguyen et al., *J Amer Coll Cardiol: Clin EP* 2015). This concept has also been proposed in the oncology field, where metallic particles have been used to enhance thermal destruction of cancer cells with RF (Xiao et al., 2014, and Cho et al., 2014). We sought to characterize ablation lesion formation characteristics using tissue sensitized to RF energy after treatment with different metals. We also utilized magnets to guide the distribution of systemically administered iron oxide (FeO) NPs for in vivo facilitated ablation.
Methods
Ex-Vivo Model:

Experimental protocols have been approved by the Institutional Animal Care and Use Committees of the University of Colorado. An ex vivo model consisting of viable bovine myocardium, a circulating saline bath at 37 degrees Celsius, a submersible load cell, and a deflectable sheath was assembled. The circulating bath utilized a perfusion pump designed for cardiac bypass and circulated fluid in a saline bath at a rate of 5 L per minute. A load cell was submersed in the bath and contained a section of viable bovine ventricular myocardium excised within 1 hour of experimentation. This load cell measured force applied to the overlying myocardial tissue and was used to standardize application of energy. This ex vivo model has been validated and described in further detail elsewhere (Nguyen et al., *J Cardiovasc Electrophysiol.* 2015; Olson et al., *J Interv Card Electrophysiol.*). A 4 mm non-irrigated RF ablation catheter (Biosense-Webster, Diamond Bar, Calif.) was positioned with 10 grams of force in a perpendicular position using a deflectable sheath (Agilis, St. Jude Medical).
Metal Nanoparticle Preparation:

FeO NPs are superparamagnetic, dispersed in normal saline, and are 10-15 nm in length (Nanomaterials, Inc. TX, USA). Titanium (Ti) nanoparticles are 30-50 nm in length and were obtained from US Research Nanomaterials, Inc. TX, USA. Copper nanoparticles (CuNPs) are 5-7 nm in length and are dispersed in an organic medium (SkySpring Nanomaterials, Inc. TX, USA).
Liposomal Iron Preparation:

Liposomal FeO NP was commercially obtained (Avanti Polar Lipids, Alabaster, Ala.). To prepare the formulation, the lipid components were measured in chloroform solutions of known concentration or weighed in dry solid state and dissolved in minimal chloroform. Chloroform was evaporated from the mixture using a gentle stream of nitrogen, thus leaving a thin lipid film on the walls of the bottle. The dry lipid film was dissolved in cyclohexane and then allowed to freeze at −50° C. The frozen lipid mixture was freeze-dried for approximately 20 hours. The resultant lipid cake was stored at −20° C.

Carbon coated iron nanoparticles were added to normal saline at 11.65 g iron nanoparticles to 578 mLs of 0.9% saline to create a buffer solution for hydration of the freeze dried lipid cake. The entire volume of iron nanoparticle buffer was added to the dry lipid cake for hydration. The mixture was heated to 50° C. and homogenized, bringing all solids into suspension.

After 24 hours, the suspension separated into a dark grey layer on top containing liposome-encapsulated iron nanoparticles. The combined liposomal suspension was processed through an emulsifier at 60° C. for a total of two passes to yield an effective diameter of 188.7 nm, polydispersity of 0.336. Gravimetric analysis presented a concentration of liposomal iron nanoparticles at 1.48 mg/mL.

Delivery of Radiofrequency Energy Applied to Infiltrated Myocardium:

A series of ablation lesions using low power (20 Watts) and high power (50 Watts) were created on recently excised bovine myocardium. Immediately prior to RF energy delivery, the myocardium was infiltrated using a 29-gauge hypodermic needle at a depth of 5 mm with 100 mcg of CuNP, 100 mcg of FeO, or 100 mcg of TiNPs. Separate ablation lesions on the same myocardial tissue were created using sham injection or 1 mL injections of 0.9% saline for comparison. The number of lesions applied per ventricular section depended upon the available endocardial surface. No lesions were placed over or in immediate proximity (5 mm) to papillary muscles or other lesions. Furthermore, no lesions were placed within 1 cm of section edge.

Tissue Temperature Analysis:

T-type thermocouple wires were inserted horizontally into myocardium at 3 mm and 5 mm depths and perpendicular to the ablation surface. Thermocouple analogue inputs were converted to digital signals using LabView software (version 7.0). Temperatures were recorded in a continuous fashion throughout the 60 seconds of RF application at a rate of 5 Hertz. Peak tissue temperature was defined as the maximum temperature reading during RF application. RF applications that generated steam pops were excluded from temperature curve analysis.

In Vivo Magnet-Guided Ablation:

Yorkshire pigs (n=4) were anesthetized and bilateral femoral artery access was obtained.

Porcine thigh preps were prepared bilaterally and modified from previously described canine thigh preps (Nakagawa et al., 1995). Briefly, the skin and connective tissue were dissected to expose the underlying muscle. The skin was raised to form a cradle, and heparinized, warmed porcine blood was circulated at 350 mL/min. An ablation catheter was placed perpendicular to the muscle surface. Ablations were delivered at 30 W for 20 seconds with the same amount of force, as measured by a force-sensing, open irrigated tip RF catheter (SmartTouch Thermocool, Biosense-Webster, Diamond Bar, Calif.); ablation lesions were tagged by the electroanatomic mapping system and averaged between 10-20 grams of force. Animals were pre-treated with 10 mg of dexamethasone and 100 mcg of epinephrine to prevent potential FeO-induced anaphylaxis and hypotension. During ablation, infusion of 200 mg FeO NPs (dispersed in 20 ml and infused at 1 ml/second) was performed via the ipsilateral femoral artery. In addition, magnets (Neodymium with 310 pound pull force, CMS Magnetics, Inc, TX, USA) were placed adjacent to the thighs near the region of ablation.

In Vivo Ablation after Liposomal Infusion:

In separate thigh preps, and prior to liposomal iron infusion, intravenous dexamethasone was given to prevent possible anaphylactic reaction to the liposomes. Control ablations, using an irrigated catheter at 30 W for 60 seconds with 10-20 grams of force, were performed on thigh preps prior to infusion of liposomes. Next, liposomal iron (10 mg/ml) was infused at a rate of 1 ml/min for 30 minutes prior to ablation. Ablation was then performed on thigh preps using the same parameters as control ablations. Ablation lesion data, including force, impedance, and power were recorded by the electroanatomic mapping system.

Magnetic Resonance Imaging:

After animals were sacrificed, thigh preps were resected and placed in 0.9% saline for immediate imaging. MRI imaging was performed using a 3.0T Skyra (Siemens Medical, Erlangen, Germany) to identify scar and iron deposition. Susceptibility weighted imaging was performed using a swi3Dlr sequence with TR 28 ms and TE of 20 ms at a field of view of 270×384 mm and slice thickness of 1.2 mm to assess for Fe deposition. Using this method, tissue injury appears as bright signal intensity, and Fe deposition appears dark; specific characteristics related to ablation can thus be assessed.

Histology and Microscopy:

Tissue containing the control and FeO ablation lesions were collected immediately after ablation and snap-frozen in liquid nitrogen. The tissue was sectioned, at 50 um thickness, using a microtome and then fixed with 10% buffered formalin. Sections were then stained with Prussian blue and counterstained with nuclear fast red. A Zeiss Axiovert 200 M microscope (Carl Zeiss MicroImaging, Inc., Thornwood, N.Y., USA) was used for imaging.

Ablation Lesion Volume Measurements:

Tissue sections were analyzed and lesions were measured with a digital micrometer. For each lesion, maximum depth (A), maximum diameter (B), depth at maximum diameter (C), and lesion surface diameter (D) were measured. Single lesion volumes were then calculated using the equation for an oblate ellipsoid (A=maximum depth, B=maximum diameter, C=depth at maximum diameter and D=lesion surface diameter):

$$Lesion Volume = \left[0.75\pi\left(\frac{B}{2}\right)^2 (A-C)\right] - \left[0.25\pi\left(\frac{D}{2}\right)^2 (A-2C)\right]$$

Statistical Analysis:

SPSS software was used to perform all calculations. The Analysis of Variance (ANOVA) test was used to compare continuous variables, and the Chi-square test was used for dichotomous comparisons of ablation lesion characteristics from metal NP treated vs. untreated tissue.

Results

Effect of Metal NP Infiltration on Ablation Lesion Characteristics and Electrical Properties Using Low and High Power Radiofrequency Energy:

At both low and high powers, ablation lesions in myocardium treated with either CuNP, FeO, or TiNP were significantly larger compared to tissue infiltrated with saline. Table 1 shows the differences in ablation lesion characteristics, using high power RF (50 W) applied to the different myocardium treatments. Ablation after metal NP infiltration resulted in larger impedance changes compared to ablation of tissue infiltrated with untreated (sham) or saline.

TABLE 1

Myocardial Ablation Lesion Characteristics After Radiofrequency Energy Applied at 50 W for 60 Seconds.

| | | Average Max Depth (mm) | Diameter Max (mm) | Max Surface Diam (mm) | Steam Pop | Volume (mm³) |
|---|---|---|---|---|---|---|
| Sham | (n = 30) | 6.0 ± 0.3 | 10.8 ± 0.8 | 6.5 ± 0.4 | 4/98 | 267.5 ± 43.7 |
| NS | (n = 30) | 6.1 ± 0.2 | 10.7 ± 0.6 | 7.5 ± 0.9 | 2/66 | 261.6 ± 31.8 |
| 100 mcg Cu | (n = 30) | 7.2 ± 0.4 | 11.7 ± 0.6 | 8.6 ± 0.5 | 5/47 | 355.7 ± 45.4 |
| 100 mcg FeO | (n = 30) | 6.3 ± 0.4 | 11.4 ± 1.1 | 7.5 ± 0.8 | 3/48 | 302.5 ± 56.2 |
| 100 mcgTi | (n = 30) | 6.7 ± 0.4 | 11.1 ± 0.8 | 7.8 ± 0.8 | 2/50 | 311.5 ± 41.9 |
| | NS vs. Sham | p = 0.092 | p = 0.671 | p < 0.001 | p = 0.725 | p = 0.556 |
| | 100 mcg Cu vs. Saline | p < 0.001 | p < 0.001 | p < 0.001 | p = 0.098 | p < 0.001 |
| | 100 mcg FeO vs. Saline | p = 0.014 | p = 0.008 | p = 0.890 | p = 0.407 | p = 0.001 |
| | 100 mcg Ti vs. Saline | p < 0.001 | p = 0.045 | p = 0.105 | p = 0.777 | p < 0.001 |

FIG. 1 details the mean starting and ending impedance measurements in untreated control (sham), saline-infiltrated, and metal NP treated myocardial tissue before and after RF ablation at 50 W.

Effect of Metal NP Infiltration on Myocardial Tissue Temperature Dispersion:

For all metals, the peak temperatures recorded at the ablation catheter tip were significantly higher in metal-treated myocardium, compared to saline infiltrated myocardium using power-control mode, at both 20 W and 50 W. When measuring temperatures at 3 mm and 5 mm depths, there were greater tissue temperatures in CuNP and FeO treated tissues, when compared to sham or saline infiltrated tissue (Table 2). FIG. 2 displays the mean temperature dispersion at 3 and 5 mm depths in FeO NP treated myocardium compared to saline infiltration and untreated myocardium after RF at 50 Watts.

TABLE 2

Mean Maximum Temperature Dispersion at 3 and 5 mm Depths for 20 Watts and 50 Watts

| | 20W | | 50W | |
|---|---|---|---|---|
| | 3 mm Depth Peak Temp | 5 mm Depth Peak Temp | 3 mm Depth Peak Temp | 5 mm Depth Peak Temp |
| Untreated | 58.5 ± 3.8 | 50.1 ± 3.0 | 74.0 ± 3.5 | 63.9 ± 2.8 |
| Saline | 59.5 ± 3.9 | 51.7 ± 2.9 | 74.7 ± 3.8 | 64.0 ± 1.8 |
| 100 mcg FeO | 61.2 ± 3.6 | 53.2 ± 3.1 | 77.9 ± 4.3 | 67.1 ± 4.5 |
| 100 mcg Cu | 64.9 ± 3.7 | 56.0 ± 3.4 | 81.2 ± 2.6 | 69.8 ± 2.8 |
| Saline vs. Untreated p-value | p = 0.501 | p = 0.174 | p = 0.593 | p = 0.927 |
| 100 mcg FeO vs. Saline p-value | p = 0.243 | p = 0.207 | p = 0.039 | p = 0.027 |
| 100 mcg Cu vs. Saline p-value | p < 0.001 | p = 0.001 | p < 0.001 | p < 0.001 |

In vivo FeO Delivery to Ablation Sites Within Thigh Preparations: Liposomal iron and FeO NPs were directed to an area of interest using magnets, as shown by the video (FIG. 3 and Video, Supplemental Materials). Staining of ablation lesion sections from porcine thighs also confirmed the presence of iron within tissues ablated after FeO infusion. The levels of iron were significantly greater (arrow) than the background iron staining (from ruptured red blood cells) of control sections (FIG. 4). In addition, MRI imaging immediately after ablation procedures also demonstrated that iron was preferentially deposited in tissue adjacent to which a magnet had been applied at the time of ablation, and within the ablation target areas. FIG. 5A shows iron deposition at the thigh preparation surface and at a depth of 5 mm from the thigh preparation surface. Iron susceptibility appears dark on MRI, within areas of ablation where magnets were placed after systemic liposomal iron infusion. These dark areas were mostly absent in areas ablated after systemic liposomal iron was infused but magnets were not applied (FIG. 5B).

In Vivo Ablation Facilitated by Iron Delivered Directly or Via Iron-Containing Liposomes:

Iron delivered via FeO NP infusion in the ipsilateral femoral artery during porcine thigh ablation with irrigated-tip catheters, and directed by magnets to the areas of ablation, led to larger ablation lesions compared to untreated controls (201.5 ml vs. 139.1 ml, p<0.001). Table 3 provides ablation lesion characteristics for control and magnet-guided FeO NP infusion.

TABLE 3

Ablation Lesion Characteristics After Irrigated-Tip Radiofrequency Energy Applied at 30 W for 20 Seconds (In Vivo Thigh Preparations and Iron Infusion)

| | | Average Max Depth | Diameter Max | Max Surface | Volume |
|---|---|---|---|---|---|
| Untreated | (n = 22) | 4.4 ± 0.6 | 9.6 ± 0.8 | 7.1 ± 0.9 | 139.1 ± 30.8 |
| FeO | (n = 22) | 5.3 ± 0.8 | 10.5 ± 1.3 | 7.8 ± 1.0 | 201.4 ± 59.3 |
| p-value | FeO vs. Untreated | p < 0.001 | p = 0.005 | p = 0.026 | p < 0.001 |

Irrigated-tip ablation following iron delivery via systemic liposomes, also led to larger lesions compared to control (379.7 ml vs. 189.5 ml, p<0.001), and lesion characteristics are summarized in Table 4.

TABLE 4

Ablation Lesion Characteristics After Radiofrequency Energy Applied at 30 W for 60 Seconds (In Vivo Thigh Preparation and Liposomal Iron Infusion)

| | | Average Max Depth (mm) | Diameter Max (mm) | Max Surface Diam (mm) | Volume (mm³) |
|---|---|---|---|---|---|
| Untreated | (n = 20) | 5.2 ± 0.7 | 10.1 ± 1.1 | 7.5 ± 1.0 | 189.5 ± 54.5 |
| Liposomal iron | (n = 23) | 7.1 ± 1.1 | 13.1 ± 1.5 | 9.1 ± 1.5 | 379.7 ± 114.8 |

TABLE 4-continued

Ablation Lesion Characteristics After
Radiofrequency Energy Applied at 30 W for 60 Seconds
(In Vivo Thigh Preparation and Liposomal Iron Infusion)

|   |   | Average Max Depth (mm) | Diameter Max (mm) | Max Surface Diam (mm) | Volume (mm$^3$) |
|---|---|---|---|---|---|
| p-value | Liposomal iron vs. Untreated | p < 0.001 | p < 0.001 | p < 0.001 | p < 0.001 |

Discussion

Study Results:

We have shown that a low dose of metallic nanoparticles (100 mcg) infiltrated directly into myocardial tissue significantly altered tissue properties and the effects of applied radiofrequency ablation energy. Specifically, in our experiments, ablation of myocardial tissue infiltrated with metal NPs resulted in an increase in ablation lesion size, a larger reduction in electrical impedance, and improved thermal conductivity. In vivo, magnets were able to guide FeO NPs and iron-containing liposomes to the site of targeted ablation, resulting in iron facilitated ablation with increased lesion sizes.

Mechanism of Metal Nanoparticle Facilitation of Radiofrequency Ablation:

In our ex vivo model, infiltration of myocardial tissue with metallic NPs resulted in significantly larger ablation lesions. There are several potential mechanisms for metallic NP facilitation of RF ablation. Copper, iron, and titanium are metals that can conduct electricity with extremely high efficiency, thereby allowing for deeper penetration of RF current through the circuit established by the catheter and grounding patch. In addition, these metals exhibit extremely efficient thermal conductivity, thereby transmitting heat and enhancing thermal injury in tissue receiving RF energy. Finally, the metallic NPs themselves can absorb RF energy remotely, thus resulting in additional heating when RF energy is applied near tissue containing them. This unique combination of favorable electrical and thermal conductive properties enhances the thermal injury to myocardial tissue treated with metallic NPs when radiofrequency energy is applied to it.

Prior Investigations into Ablation of Nanoparticle Treated Tissue:

We have previously demonstrated that RF ablation near metallic objects can lead to collateral heating near the metal (Nguyen et al., Heart Rhythm, 2015). We demonstrate here that a similar phenomenon can be utilized to enhance ablation efficacy.

Studies in cancer therapeutics have utilized various metals to improve thermal energy destruction of tumor cells. We first applied this concept to cardiac ablation using carbon nanotubes (CNTs), which are not metallic but can thermally conduct RF (Nguyen et al., 2014). The use of CNTs in humans has not been demonstrated and we therefore explored the use of gadolinium, a commonly used chelated metal in medical procedures, to facilitate ablation (Nguyen et al., J Amer Coll Cardiol: Clin EP 2015). We showed that ablation after in vivo injection of gadolinium led to increased lesion sizes in a porcine model.

However, the high doses of gadolinium that would need to be directly injected in order to achieve sufficiently high myocardial distribution may limit its widespread utility (Sacher et al., 2015). Hence, in this study, we demonstrated that small amounts of metals in the bloodstream can enhance ablation lesion sizes, allowing for the possibility of systemic administration. We further established that a novel strategy using magnetic guidance can effectively direct distribution of metal NPs to a targeted site of ablation. Iron was chosen to facilitate ablation since it has been used in humans, and FeO NPs have been studied in cancer therapeutics (Rejinold et al., 2015, and Bañobre-López et al., 2013). In addition, magnetic guidance of nanoparticles has been previously shown as a viable drug delivery system, including its use to direct ganglionic plexus toxicity (Yu et al., 2010). Heat-sensitive liposomes can be utilized to systemically administer a pharmacologic payload but yet have a localized effect by only releasing that payload upon heat activation. Liposomes are biologically inactive and have minimal toxic effects. By encasing iron nanoparticles within a liposome, systemic side effects can be prevented. Magnetic navigation of the FeO liposomes further enhances the localized effect of the metallic agents on ablation lesion formation. Our study demonstrates the potential utility of heat sensitive liposomal agents for augmenting RF ablation.

Clinical Implications for Metal NP "Facilitated Ablation":

The goal of our study was to explore the possibility of improving the efficacy and safety of cardiac ablation using metal NPs and specifically FeO in vivo. The use of metal NPs in myocardial tissue offers promise in other aspects of electrophysiology. In order to realize the clinical potential for copper or titanium facilitation of RF ablation, a reliable delivery mechanism into targeted myocardial tissue is needed. These agents lack the high level of ferromagnetism of iron and therefore other strategies, outside of magnetic guidance, would need to be explored to concentrate these agents into targeted tissue. Potential methods for copper or titanium delivery into targeted myocardium include direct injection into tissue, use of heat sensitive liposomes, infusion into coronary arteries or veins overlying targeted tissue, and induction of cellular uptake by functionalizing metallic NPs through their binding to specific agonists for cardiac-specific receptors. Further research into developing these potential strategies for metallic NP delivery into the myocardium is essential for the exploration of the clinical application of our observations.

This study used bovine myocardium in an ex vivo model and a porcine thigh preparation in an in vivo model to approximate radiofrequency ablation lesion characteristics produced during indicated procedures performed in patients with cardiac arrhythmias.

Summary

In both ex vivo and in vivo models, myocardial exposure to metallic NPs resulted in enhanced sensitivity to the thermal destruction of tissue from applied radiofrequency energy. Metallic NPs significantly altered the electrical properties of targeted myocardial tissue and resulted in an increased sensitivity to RF heating. Furthermore, metallic NP facilitated RF ablation of targeted tissue through ohmic heating of the NPs themselves and through improved thermal conductivity, resulting in larger ablation lesions compared to untreated tissue. Metallic NPs can also be directed using magnetic guidance for targeted ablation.

Example 2

Local Inhibition of Heat Shock Protein Response to Improve Precision and Durability of Radiofrequency Ablation Lesions for the Treatment of Cardiac Arrhythmias Introduction Low-level exposure to thermal injury leads to up-regulation of protective cellular pathways, mediated in part by heat shock proteins (HSPs), to prevent apoptosis, which can render the tissue resistant to subsequent heat exposure. Administration of HSP inhibitors concurrent with ablation may improve lesion durability and potentially enhance ablation lesions without requiring higher RF power that is associated with complications. Further, HSP inhibitors can decrease heterogeneity at the border zones surrounding targeted tissue and myocardial infarct scar after RF, thereby decreasing post-RF ablation arrhythmia susceptibility. Liposomes encapsulating metallic nanoparticles (MNPs) may be magnetically guided to an RF ablation site to improve precision of RF power delivery. Local delivery of therapeutic agents using liposomes is an emerging field in oncology. Magnetic guidance of MNP encased liposomes may be used to precisely deliver pharmacotherapeutics to targeted myocardial tissue. Furthermore, released MNPs are expected to amplify the effect of ohmic heating at the targeted site.

HSP inhibitors with MNP encased liposomes may be used to magnetically guide HSP inhibitors for targeted drug delivery to improve both the precision and durability of RF ablation of myocardial tissue. A porcine atrial fibrillation ablation (AF) model, whereby the pulmonary veins (PVs), which are the predominant source triggering AF, are electrically isolated using RF ablation from the left atrium can be utilized. Pulmonary vein isolation is the cornerstone of AF ablation today, but when the PVs lose isolation (become electrically re-connected), this is a major cause of AF recurrences after ablation. In this model, ablation after MNP-guided delivery of HSP inhibitors may lead to improved ablation lesions and decreased pulmonary vein (PV) re-connections and therefore decreased AF recurrences.

Background and Significance

Well over several hundred thousand procedures using RF ablation are performed annually in the US to treat cardiac arrhythmias. However, there are significant limitations that impact the efficacy and safety of this procedure. One such limitation is the inability to achieve durable lesions with the safe delivery of low power to myocardial tissue. Furthermore, there are risks of "steam pops," cardiac perforation, and unintended injury to anatomically adjacent structures when higher levels of energy are used.

RF Facilitation.

Studies in cancer therapeutics have utilized various facilitating agents, including non-toxic metals, to improve thermal energy destruction of tumor cells (Cardinal, et al., 2008; Cho, et als., 2014). We first applied this concept to cardiac ablation using carbon nanotubes (CNTs), which can thermally conduct RF and increase myocardial lesion sizes (Nguyen, et als., 2014). The use of CNTs in humans has not been demonstrated and we next explored the use of gadolinium, a commonly used metal in medical imaging, to facilitate ablation. We showed that ablation after in vivo injection of gadolinium in a porcine model resulted in larger lesions (Nguyen, et als., 2015). However, the delivery method of direct injection for gadolinium to achieve sufficiently high doses can limit its utility (Sacher, et al., 2015). In addition, these strategies simply potentiated RF destruction, which continue to carry risks of complications due to stronger RF energy and would also remain grossly imprecise in tissue destruction.

Heat Shock Proteins.

RF ablation leads to thermal destruction within a core of tissue necrosis where temperatures are greater than 50 degrees Celsius (Haines, 2004). However, peripheral to this necrotic core are tissues that have been subjected to sub-lethal thermal injury and reversible changes and may therefore appear electrically inactive during and immediately after the ablation procedure. This tissue with dormant conduction will eventually regain electrical conduction capability up to several months later, resulting in post-ablation arrhythmia recurrences and the need for a repeat procedure. Further RF ablation during the same ablation session or in subsequent attempts may not result in complete destruction of targeted tissue due to edema, anatomic limitations, or because it may cause collateral injury to vital structures, such as the esophagus, phrenic nerve, or specialized conduction system.

The cellular response to this sub-lethal thermal injury within the ablation periphery is complex and multifaceted. Cellular stress leads to up-regulation of oxidative pathways that induce apoptosis. Counterbalancing these stressors are reparative pathways that have cellular protective effects against apoptosis, especially the production of heat shock proteins in response to thermal injury. HSPs can ameliorate apoptosis through a variety of mechanisms, including inhibition of procaspase 9 activation, prevention of cytochrome c release from mitochrondria, and JNK phosphorylation (Polla, et als., 1996; Xanthoudakis, et al., 2000; Gabai, et als., 2000).

Several pharmacologic agents known to have anti-HSP effects have been used in clinical oncology as part of a strategy to eliminate tumors. Paclitaxel has suppressive effects on HSP activity leading to apoptosis. It has been used in conjunction with RF heating to treat breast adenocarcinoma tumors in a rat model (Zhao, et als., 2010). Quercetin is a naturally occurring flavonoid agent that has known inhibitory effects on HSP production. HSP gene expression is inhibited by quercetin via down-regulation of heat shock transcription factors and prevention of initiation and elongation of the HSP70 mRNA (Hansen, et als., 1997; Lee, et als., 1994). Quercetin has been used in combination with RF to increase tumor destruction in a rodent model of adenocarcinoma tumor. Animals treated with combined quercetin and RF energy had decreased HSP expression, increased apoptosis, and larger tumor destruction (Yang, et als, 2011).

Liposomes and Drug Delivery.

Heat-sensitive liposomes can be utilized to systemically administer a pharmacologic payload but yet have a localized effect by only releasing that payload upon heat activated phase change. Liposomes are biologically inactive and have minimal toxic effects. By encasing an agent within a liposome, one can prevent systemic side effects as well as protect the drug from being degraded until it reaches its heated target. Strategies employing heat-sensitive liposomes have been used successfully in humans to deliver chemotherapeutic agents (Rivera, et als., 2003; Gordon, et als., 2000). Most water-soluble drugs, including paclitaxel and quercetin, can be encased within the inner aqueous compartment of liposomes.

Magnetic guidance of nanoparticles has been previously shown as a viable drug delivery system, including its use to direct ganglionic plexus toxicity (Yu, et als., 2010). Iron is a non-toxic metal that has been used in a nanoparticle formulation in humans as a magnetic resonance imaging agent, and iron oxide (FeO) NPs have been studied in cancer therapeutics (Rejinold, et als., 2015; Bañobre-López, et als., 2013). We have been able to encase FeO NPs within liposomes and have demonstrated their successful intravascular navigation using a magnetic field over an animal thigh preparation. While RF heating has been shown to release drug payloads from liposomes, magnetic navigation of MNP encased liposomes to the heart has not been previously demonstrated. Therefore, we sought to couple anti-HSP agents with FeO NPs within liposomes in order to magnetically guide these liposomes to targeted myocardium and demonstrate improved ablation lesion characteristics.

Significance.

The impact of improved RF lesion durability and precision for the treatment of cardiac arrhythmias cannot be overstated. While RF ablation has become an effective treatment for most arrhythmias, recurrence rates for certain arrhythmias remain unacceptably high, leading to repeat procedures, increasing morbidity, and even death. Recurrences after AF and VT ablations can be 50% or higher, and the lack of lesion durability or anatomic limitations play a large role for these recurrences. Furthermore, a continued trend in the ablation field is to use ablation catheters and strategies designed to deliver more RF power. If more RF power is not sufficient, then more extensive ablation is deemed to be required. However, more power delivery or more extensive ablation has significant risks of complications and the potential for pro-arrhythmia, thus compromising safety while still failing to be effective.

A mechanistic approach to improve RF efficacy and safety by targeting the cellular response to RF heating while improving precision of ablation using targeted drug delivery with magnetic guidance is presented namely focusing on the tissue response to RF heating and on directed drug delivery at the time of RF and not simply on the ablation power being applied.

Preliminary Studies

In Vivo Liposome Delivery to Ablation Sites within Thigh Preparations.

Liposomal FeO NPs can be directed to an area of interest using magnets, as depicted in FIG. 1, where a magnet is attracting FeO-containing liposomes against gravity.

An in vivo porcine thigh model was used to study FeO NPs, which were delivered systemically within heat sensitive liposomes and guided by magnets. Ablation was performed with a force-sensing irrigated catheter and recorded using an electroanatomic mapping system. Magnetic resonance imaging (MRI) and pathologic staining of thighs were subsequently performed.

Magnetic guidance of liposomal FeO NPs to porcine thigh preps was demonstrated by MRI. FIG. 5A shows iron deposition, which appears dark on MRI (arrows), within areas of ablation where magnets were applied after liposomal iron infusion. These dark areas were absent in areas of ablation where no magnets were used (FIG. 5B).

Furthermore, staining of ablation lesion sections from porcine thighs also confirmed the presence of iron within tissues ablated after magnets directed FeO NPs to the ablation sites The levels of iron are significantly greater (FIG. 4A, white arrow) than the background iron staining (from ruptured red blood cells) of control sections (FIG. 4B).

RF after liposomal delivery of FeO NPs enhanced ablation lesions, which were larger in volume than control lesions, 379.7 ml vs. 189.5 ml ($p<0.001$), indicating enhanced ohmic heating of the tissue from the presence of FeO. Hence, FeO within liposomes can be used to magnetically direct liposomes but are also augmenting RF ablation due to the alterations in tissue resistivity and remote metallic heating within the tissue. This is consistent with our prior research demonstrating remote metal heating located near a RF ablation source, a phenomenon that can be harnessed to extend local RF heating and increase lesion sizes (Nguyen, et als., *Heart Rhythm,* 2015).

Ablation Biophysics.

We have both ex vivo and in vivo models, including porcine thigh preparations and endocardial and epicardial ablation models, as well as post-myocardial infarction models.

We have shown that partial insulation of ablation catheters can improve both efficacy and safety of ablation. In an epicardial porcine ablation model, partial insulation protected the pericardium from collateral ablation while enhancing ablation lesion sizes of the epicardium (Nguyen, et als., *Heart Rhythm,* 2015; 12:623-630). We have also demonstrated that, in irrigated ablation, decreasing the irrigant osmolarity and charge density can increase RF energy delivery to tissue, resulting in larger lesions for both open and closed irrigated ablations (Nguyen, et als., *J Cardiovasc Electrophysiol,* 2015).

Although the principle of remote metal heating can be utilized to improve RF delivery, as illustrated with liposomal FeO delivery to in vivo thigh preparations and with myocardial ablation after direct gadolinium injection, we also have shown that this principle can raise safety concerns. RF ablation near metallic cardiac devices and un-insulated metallic objects such as esophageal temperature probes can lead to ohmic heating of surrounding tissues and potentially unintended collateral injury (Nguyen, et als., *Heart Rhythm,* 2015).

Research Design and Methods

We will use our rodent model of ablation to study the HSP response to ablation and how it can be modulated at the time of RF ablation. Assays for apoptosis and HSP will be performed for standard RF at various powers and for RF after treatment with HSP inhibitors (quercetin). Two time points will be studied—2 hours after RF (acute) and 4 weeks after RF (chronic)—to determine when HSP inhibition has the largest impact on RF myocardial ablation. Optical mapping will be used to evaluate conduction velocities and electrical heterogeneity in RF border zones, while histology will be used to quantify RF lesion sizes and to assess for fibrosis in RF border zones.

Rodent Ablation Model.

After baseline echocardiography, 120 male Sprague-Dawley rats, ages 6-10 weeks, will undergo RF ablation, as modified from Antonio et al 2009 (Antonio, et als., 2009). Under anesthesia and after a left thoracotomy and pericardiotomy are performed, RF ablation lesions (1 per rat) are created in unipolar mode using a custom-made catheter with a single electrode located at its tip, and RF delivery is delivered against an indifferent electrode with a large area. For controls, RF is delivered on the left ventricular (LV) free wall in power control at 5 Watts (n=20), 10 Watts (n=20), and 15 Watts (n=20) for 10 seconds using a standard ablation generator (Stockert, Freiberg, Germany). Antonio et al. have shown that a 12-Watt (W) ablation for 10 seconds will create a non-lethal, sizable myocardial lesion (Martinelli, et als., *ACS Nano*). Animals are sacrificed, and hearts are harvested after 2 hours (n=10 in each power group, acute) and after 4 weeks (n=10 in each power group, chronic). Echocardiography is performed at 4 weeks. The same number of animals and groups are repeated for quercetin-treated animals.

Liposomal Quercetin.

Quercetin-loaded liposomes are prepared commercially (Avanti Polar Lipids, Alabaster, Ala.). Briefly, as previously described (Yang, et als., 2011), liposomes encapsulating quercetin were prepared with 0.29 mg of quercetin (1 mg/mL solution in methanol), which was added to hydrogenated soy phosphatidylcholine, cholesterol and polyethyleneglycol phosphatidylethanolamine (PEG2000-PE) (57.25:37.57:5.18 mol %, respectively) solutions in chloroform. A lipid film was created after removal of solvent on a rotary evaporator; this lipid film was then rehydrated with 1 mL of phosphate buffered saline, pH 7.4, and the preparation was probe-sonicated with a sonic dismembrator at an output of 7 W for 30 min. Quercetin was loaded at 5 mol % into liposomes. Liposomal quercetin is given slowly 1 hour prior to RF and infused for 30 sec via tail vein injection at a dose of 0.29 mg in 0.5 mL. This dose was studied by Yang et al 2011 and they found a statistically significant effect for RF in combination with quercetin in improved tumor destruction with an n=6 in each group (Yang, et als., 2011).

We will use our rodent myocardial infarction (MI) model to study how HSP modulation during ablation of infarct scar can impact the heterogeneity of infarct border zones (IBZ) and ventricular arrhythmia susceptibility. After infarcts are created, we will deliver standard RF, at various powers, to the infarcts, with and without quercetin pre-treatment. Two time points will be studied—2 hours after and 4 weeks after RF ablation of myocardial infarcts. We will use optical mapping to assess conduction velocities and heterogeneity of the infarct zones, IBZs, and non-infarcted tissues.

Rodent Myocardial Infarct Models:

Our lab has experience with the rodent model of MI, with a 50%-70% induction of ventricular arrhythmias after MI (Ding, et als.; Nguyen, D T, Ding, C, et als., Heart Rhythm). Under general anesthesia and after baseline echocardiography, 120 male Sprague-Dawley rats, ages 6-10 weeks, will undergo thoracotomy and ligation of the left anterior descending artery. This technique produces a reliable and reproducible anteroapical LV infarction. The thoracotomy is closed, and animals are followed for 4 weeks when echocardiography is repeated and another thoracotomy is performed under general anesthesia. RF is delivered on the left ventricular (LV) free infarct scar in power control at 5 Watts (n=20), 10 Watts (n=20), and 15 Watts (n=20) for 10 seconds using a standard ablation generator (Stockert, Freiberg, Germany). Animals are sacrificed, and hearts are harvested after 2 hours (n=10 in each power group, acute) and after 4 weeks (n=10 in each power group, chronic). The same number of animals and groups are repeated for animals treated with quercetin, which is infused (0.29 mg in 0.5 mL) 1 hour prior to RF of their infarcts.

Electrophysiology (EP) studies and optical mapping, as outlined below, will be performed for all experimental groups to assess for differences in effective refractory periods (ERP), heterogeneity of conduction velocities, dispersion of repolarization, and ventricular arrhythmia vulnerability. Ventricular tissues will be processed for immunoblotting and histology studies.

Optical Mapping (OM):

Animal hearts will be excised and retrogradely perfused in a Langendorff preparation. Before optical recordings, Tyrode solution containing voltage-sensitive dye Pittsburgh-I will be perfused through the preparation. During optical recordings, contractility will be blocked with blebbistatin. The OM procedure is modified from previously described studies (Ding, et als.; Nguyen, D T, Ding, C, et als., Heart Rhythm). To summarize, ten thousand simultaneous optical action potentials (APs) will be recorded with a 100×100 CMOS camera within a 7 mm×7 mm mapping field on the epicardium of the LV anterior wall. Using a 1000-W tungsten-halogen light source, fluorescence will be excited with an excitation filter of 530 nm and transmitted with an emission long-pass filter of >630 nm. Fluorescent optical maps will be acquired at 1000 Hz during programmed electrical stimulation. Mapping will be recorded during pacing drives of 200 ms to 50 ms (decremented by 10 ms), as well as during S1-S2 pacing using a pacing cycle length (PCL) of 150 ms and maximum S2 of 100 ms and decremented by 10 ms until ERP. Programmed stimulation, with up to three extrastimuli, and burst pacing (from 90 ms to 40 ms) will be used to assess arrhythmia inducibility. Inducibility is defined as the ability to provoke sustained ($\geq$30 seconds) VT or ventricular fibrillation.

Data Analyses:

OM data will be analyzed using OMproCCD software (courtesy of Bum-rak Choi, Providence, R.I.). Raw fluorescence data will be viewed as a movie of normalized fluorescence intensity, which will reveal activation within the field of view. Quantitative data will then be obtained from optically derived APs for each of the 10,000 pixels of the CMOS camera. Activation time and AP duration at 80% repolarization (APD80) will be measured for each PCL. Activation time will be calculated at the maximum rate of rise of the fluorescent AP (dF/dt). APD80 will be measured as duration from activation time (start of AP) to the time point where the AP had recovered to 20% of the maximal fluorescent signal. Isochronal maps of activation will be constructed for each animal. Rise time will be calculated as the time between takeoff (maximum value of the second derivative) and the peak of the AP.

The OMproCCD software will be used to calculate conduction vectors representing local conduction velocities (CVs) and directions at each pixel (Salama, et als., 1994). Phase differences, calculated as the average difference with neighboring activation times at each site, will be measured to quantify the spatial heterogeneity of conduction, as previously described (Lammers, et als., 1990). Frequency histograms will be constructed for phase differences within a recorded area. These histograms will be summarized as the median phase time at $50^{th}$ percentile (P50), and the 5th and 95th percentiles (P5 and P95, respectively) of the distribution. The heterogeneity range will be quantified as the width of the distribution, P95-P5, while conduction heterogeneity index will be defined as the heterogeneity range divided by the median phase, or (P95-P5)/P50.

For each sample, a variety of EP parameters will be determined for RF core zone (non-MI animals), RF border zone (non-MI animals), infarct zone, infarct border zone, and un-affected myocardium. Parameters include conduction velocities, conduction heterogeneity index, action potential duration, AP rise, AP rise time, AP amplitude, VT/VF inducibility, effective refractory periods, and ECG intervals. These will be correlated to their treatment groups (non-infarct, RF alone vs. RF+quercetin; infarct, RF alone vs. RF+quercetin), infarct size, infarct border zones, and amount of HSP/apoptosis. Furthermore, optical mapping will allow us to analyze the types of VT/VF that are induced, including their initiating and sustaining mechanisms.

Echocardiography:

Serial echocardiography will be performed at baseline and at 4 weeks after RF or infarction, using a high-resolution echocardiographic system (Vevo 660, VisualSonics, Toronto, Canada) equipped with a 25-MHz mechanical transducer. Parasternal long-axis and short-axis views were acquired. Using the long-axis view, LV end-systolic and end-diastolic volumes (ESV and EDV), as well as LV ejection fraction (LVEF), were calculated. The system software utilizes a formula based on a cylindrical-hemiellipsoid model (volume=8*area²÷3÷length) (Zhang, et als., 2007). LVEF was calculated using the formula: (EDV-ESV)/EDV*100.

Histological, Immunoblotting, and Immunohistochemistry Studies:

For each subgroup above, ventricular tissue samples will be fixed in 10% formalin. Samples will be embedded in paraffin, sectioned (4- to 5-μm thick), and stained with hematoxylin and eosin, Masson's trichrome, or Sirius red. Slides will be analyzed for fibrosis; ablation and/or infarct size will be quantified from digital photomicrographs of Sirius red-stained sections (Nguyen, DT, Ding, C., et als., *Heart Rhythm*). Ventricular tissue samples will also be frozen in liquid nitrogen for immunoblotting studies of cytokines using standard techniques. Cytokines of interest include those that potentially play an important role in the healing process (i.e., mediators of inflammation or fibrosis development), including NF-κB, TNFα, IL-6, interleukin-1 family members, C-reactive protein, platelet-derived growth factor (PDGF), and transforming growth factor β1 (TGFβ1) (Leask, 2007).

Immunohistochemistry will also be performed using antibodies to cleaved caspase-3, a marker of apoptosis (Liu, et als., 2009) (Cell Signaling Technology, Danvers, Mass.), and Hsp70, a key product of the HSP chain (Stressgen, Chicago, Ill.) (Thériault, et als., 2006). Nuclear counterstaining is performed lightly with hematoxylin. Specimen slides are imaged and analyzed using a Zeiss Axiovert 200 M microscope (Carl ZeissMicroImaging, Inc., Thornwood, N.Y., USA). Quantitative analysis is performed by measuring the percentage of cells that stain per high-powered field (hpf, 40×) within selected areas in the border zones surrounding the RF core zones and/or infarcts.

Expected Results.

We expect that HSP inhibitors such as quercetin will increase RF ablation lesions, even at low powers, and that there will be less heterogeneity at RF border zones (BZ). We further expect that RF ablation of myocardial infarcts, in combination with quercetin, will lead to improved scar homogenization, less heterogeneity of infarct border zones, and less arrhythmia susceptibility.

solution. The combined liposomal suspension is processed through an emulsifier at 60° C. with a concentration of liposomal FeO NPs at 1.48 mg/mL.

In Vivo Magnet-Guided Ablation.

Yorkshire pigs (n=10) are anesthetized and intravenous lidocaine (50-100 mg) and amiodarone (150 mg IV) are used intraoperatively for prophylaxis of ventricular arrhythmias. The left ventricle (LV) is accessed using a retrograde aortic approach after femoral arterial access is obtained. Epicardial access is obtained in the same specimen under fluoroscopy using a 17-gauge Pajunk needle (Pajunk Medical Systems, Norcross, Ga.), and a 9 French sheath is placed in the epicardium. An electroanatomic map of the entire endocardium and epicardium is created using the CARTO3 mapping system (Biosense-Webster, Diamond Bar, Calif.).

Endocardial and epicardial ablations are delivered at 30 W for 60 seconds with the same amount of force as measured by SmartTouch technology on the open irrigated tip RF catheters (Biosense-Webster, Diamond Bar, Calif.); ablation lesions are tagged by the electroanatomic mapping system. The LV endocardium and epicardium are divided into quadrants; control ablations and ablations after magnet-guided liposomal FeO are performed in each quadrant.

Prior to liposomal iron infusion, intravenous dexamethasone is given to prevent an anaphylactic reaction to the liposomes. Liposomal FeO NPs (10 mg/ml) is then infused at a rate of 1 ml/min for 30 minutes prior to ablation (optimal dosing derived from our thigh preparation studies). Control ablations (n=5 pigs), using an irrigated catheter at 30 W for 60 seconds with 10-20 grams of force, are performed in each quadrant of the LV endocardium and epicardium. In 5 pigs, magnets (Neodymium magnets with 310 pound pull force, CMS Magnetics, Inc, TX, USA) are placed adjacent to the heart and within proximity to the region of ablation. Ablation is then performed on the epicardium and endocardium using the same parameters as control ablations. Ablation lesions are tagged by the electroanatomic mapping system. Following ablation, animals are sacrificed and the hearts are immediately explanted and fixed in formalin. Gross pathol-

TABLE 5

Expected results for RF + quercetin treated animals, compared to RF alone.

| Non-infarct | RF Lesion Size | RF BZ Hetero-geneity | RF BZ Conduction Velocity | VT/VF Inducibility | Cleaved Caspase-3 | HSP70 |
|---|---|---|---|---|---|---|
| Acute | ↑ | ↓ | ↑ | N/A | ↑↑ | ↓↓ |
| Chronic | ↑↑ | ↓↓ | ↑↑ | N/A | = | = |

| Infarct | MI Lesion Size | Infarct BZ Hetero-geneity | Infarct BZ Conduction Velocity | VT/VF Inducibility | Cleaved Caspase-3 | HSP70 |
|---|---|---|---|---|---|---|
| Acute | = | ↓ | ↑ | ↓ | ↑↑ | ↓↓ |
| Chronic | = | ↓↓ | ↑↑ | ↓↓ | = | = |

Our preliminary results have shown that we can magnetically guide iron oxide nanoparticles (FeO NPs), encased in liposomes, to ablation sites on porcine thigh preparations. The porcine cardiac ablation model will be used to demonstrate that they can also be magnetically guided to the porcine heart during both endocardial and epicardial ablations.

Liposomal FeO Preparation.

Liposomal FeO is commercially obtained (Avanti Polar Lipids, Alabaster, Ala.). Briefly, carbon coated FeO NPs (11.65 g) are added to 578 mLs saline to create a buffer ogy is performed and ablation lesions are analyzed and correlated to electroanatomic mapping.

Magnetic Resonance Imaging.

After animals are sacrificed, hearts are explanted and placed in 0.9% saline for immediate imaging (prior to fixing in formalin for pathology). MRI scans using T2 weighted imaging is performed to identify the presence or absence of iron within the ablation lesions.

Histology and Microscopy.

Myocardial tissue containing control and magnet-guided liposomal FeO ablation lesions are collected immediately after ablation, embedded in OCT, and snap frozen in liquid nitrogen. The tissues are sectioned, at 50 um thickness, using a microtome and then fixed with 10% buffered formalin. Sections are then stained with Prussian blue and counter-stained with nuclear fast red. A Zeiss Axiovert 200 M microscope (Carl ZeissMicroImaging, Inc., Thornwood, N.Y., USA) is used for imaging.

Ablation Lesion Volume Measurements.

Lesion volumes are acquired by analyzing tissue sections with a digital micrometer. Single lesion volumes are calculated using the equation for an oblate ellipsoid. For each lesion, maximum depth (A), maximum diameter (B), depth at maximum diameter (C), and lesion surface diameter (D) are measured.

volume of oblate ellipsoid $$LesionVolume = \left[0.75\pi\left(\frac{B}{2}\right)^2(A-C)\right] - \left[0.25\pi\left(\frac{D}{2}\right)^2(A-2C)\right] \quad \text{Equation 1}$$

Where A=maximum depth, B=maximum diameter, C=depth at maximum diameter and D=lesion surface diameter Expected Results.

Similar to our preliminary data on magnet-guided liposomal FeO NPs in porcine thigh preparations, we expect that magnetic guidance of liposomal FeO NPs will result in FeO NPs being deposited in myocardial tissue at sites of ablation. As the epicardium is closer to the magnets, we expect that more FeO NPs will be deposited in epicardial ablations. We also expect larger lesion sizes compared to controls, as was observed in our thigh preparation studies.

TABLE 6

Expected results for RF + magnet + liposomal FeO, compared to RF + liposome FeO.

| Non-infarct | RF Lesion Size | MRI T2 signals | Iron stain |
|---|---|---|---|
| Endocardium | ↑ | ↑ | ↑ |
| Epicardium | ↑↑ | ↑↑ | ↑↑ |

By combining HSP inhibitors with FeO NPs into the same liposomes, we can magnetically direct HSP inhibitors to targeted sites of ablation. We will demonstrate that HSP inhibitors can be magnetically directed to sites of porcine pulmonary vein electrical isolation in our AF model and that RF ablation, in combination with targeted delivery of HSP inhibitor, will result in improved lesion durability, decreased heterogeneity in the ablation sites around the pulmonary veins, and decreased pulmonary vein re-connection.

Liposomal FeO and Quercetin Preparation.

Liposomes containing both FeO and quercetin will be commercially prepared (Avanti Polar Lipids, Alabaster, Ala.).

Porcine Pulmonary Vein Isolation Model.

A total of 45 pigs will undergo pulmonary vein isolation (15 pigs with liposomal FeO infusion+magnetic guidance, 15 pigs with liposomal FeO/quercetin infusion but no magnetic guidance, and 15 pigs with liposomal FeO/quercetin infusion+magnetic guidance). After animals are sedated, intubated, and mechanically ventilated, venous access is obtained, heparin bolus is given (to achieve ACT>300 s), and a double transseptal access is performed to access the left atrium. The swine anatomy of the right superior pulmonary vein (RSPV) is most similar to humans, and thus only this vein is targeted for electrical isolation with ablation (Gersentfeld, et al., 2010). A 10-pole circular mapping catheter (Lasso, Biosense Webster) is advanced into the RSPV to record baseline PV potentials.

In Vivo Magnet-Guided Ablation.

Prior to any ablation, intravenous dexamethasone is given to prevent an anaphylactic reaction to the liposomes. Liposomal FeO NPs (10 mg/ml) or liposomal combination of FeO NPs (10 mg/ml) and quercetin (2.9 mg/ml) are then infused at a rate of 1 ml/min for 30 minutes prior to ablation. The dose of quercetin is based on a calculated concentration of 1.45 mg/kg from the rodent studies, which have been the only animal studies to date using quercetin with RF heating.

Animals are randomized to 3 groups: magnetic guidance of liposomal FeO NPs; magnetic guidance of liposomal FeO NP/quercetin, or sham guidance of liposomal FeO NP/quercetin. Ablation operators are blinded to the randomization. A circumferential PV ablation is performed, and further ablation is continued until PV entry and exit block are achieved (PV isolation). Endocardial ablations are delivered at 20-30 W with the same amount of force as measured by Smart-Touch technology on the open irrigated tip RF catheters (Biosense-Webster, Diamond Bar, Calif.); ablation lesions are tagged by the electroanatomic mapping system. Total ablation lesions, ablation times, mean temperatures, and impedance changes will be recorded. Animals are then extubated and monitored for 4 weeks.

On follow up after 4 weeks, animals are anesthetized with ketamine/isoflurane and mechanically ventilated. The left atrium (LA) is again accessed via transseptal access. An electroanatomic map of the entire LA endocardium surrounding the RSPV is created using CARTO3 mapping system (Biosense-Webster, Diamond Bar, Calif.) and a multipolar Pentarray mapping catheter (Biosense Webster). Detailed geometries (>500 points) and voltage maps of the LA are obtained. Anatomic structures will be marked on the re-constructed image. Gaps in the ablation line, defined as any point with voltage >0.5 mV, are annotated and quantified. A circular mapping catheter is again advanced into the RSPV and PV re-connection is evaluated for the presence of electrical entrance or exit. Once electroanatomic mapping is performed and once PV re-connection, if any, is recorded, AF inducibility is assessed. Burst atrial pacing from 200 ms to 50 ms or AERP is performed. Sustained atrial fibrillation is defined as irregularly irregular atrial activity <200 ms for more than 3 minutes. Animals are then sacrificed.

Optical Mapping.

After intravenous injection of 5,000 units of heparin, pigs will be euthanized by injection of 50 mg/kg pentobarbital sodium, and hearts are rapidly excised and immersed in cardioplegic solution. The aortas are then cannulated and perfused retrogradely with cardioplegic solution. Before optical recordings, normal saline containing 200 μg of the voltage-sensitive dye di-4-ANNEPS (Molecular Probes) will be perfused through the preparation over a 15-min period.

Two-hundred fifty-six simultaneous optical action potentials will be recorded with a 16×16 photodiode array from 2×2-cm areas on the RSPV-LA circumferential border (site of LA ablation to achieve PV isolation). Fluorescent optical maps are acquired at 1000 Hz during programmed electrical stimulation. During optical recordings, contractility will be blocked with blebbistatin. After a recording location is selected, six unipolar stimulation electrodes will be inserted around the field of view. Optical maps will be recorded during drive trains with basic cycle lengths (BCLs) of 500, 400, 350, 300, 275, 250, 225, and 200 ms.

Raw fluorescence data will be viewed as a movie of normalized fluorescence intensity, which reveals activation within the field of view. Quantitative data are obtained from optically derived action potentials (APs) for each of the 256 pixels of the photodiode array. Activation time and action potential duration at 80% repolarization (APD80) will be measured for each paced cycle length. Activation time will be calculated at the maximum rate of rise of the fluorescent AP (dF/dt) (3). APD80 is the time difference between the activation time and 20% maximal fluorescent signal (peak of the optical AP). Isochronal maps of activation will be constructed for each map. Conduction vectors will be calculated for each point and phase differences, calculated as the average difference with neighboring activation times at each site, will be measured to quantify the spatial heterogeneity of conduction.

The area of slowest conduction around the RSPV-LA borders will be identified as the region with maximum crowding of isochrones; the length of the region of slow conduction will be calculated as the number of pixels within this region along the direction of the activation wave front.

Histology and Iron Stains:
As previously described above.
Statistical Analysis.

SPSS software is used to perform all calculations. Data are expressed as mean+/−SD or median. Comparisons among conditions will be performed with a 1-way ANOVA, and between group comparisons after ANOVA will be made with Scheffé's method. A 2-tailed Student t test will be performed when appropriate. Within-groups effect will be calculated by the estimated marginal means method with the Bonferroni correction for multiple comparisons. For VA vulnerability, nonparametric tests will be used: the Friedman test to evaluate the effect on each group of increasing RF powers and the Kruskal-Wallis H test for the differences between groups at each RF power. Data variables among the groups (inter-group) will be compared with the Kruskal-Wallis test, and if P was <0.05, follow-up comparisons of the different groups will be done with the Mann-Whitney test. Proportion comparisons will be performed with the Fischer exact test. Results will be presented as median (25% to 75% interquartile range). Statistical significance is defined as P<0.05.

Expected Results.

We anticipate that liposomes containing FeO NPs and quercetin will be magnetically guided to porcine RSPV-LA borders during PV isolation ablation. We expect quercetin to both augment immediate RF ablation as well as maintain RF lesion durability. This should lead to a more homogeneous RSPV-LA circumferential ablation and decreased PV reconnection rates. Magnetic guidance of liposomal FeO NPs/quercetin should have larger RF lesions, less PV reconnections, and/or less AF inducibility, compared to either magnetic guidance of FeO NPs or non-magnetic guided liposomal FeO/quercetin.

TABLE 7

Expected results for RF + liposomal FeO/quercetin + magnet, compared to either RF + liposomal FeO/quercetin (no magnet) or liposomal FeO + magnet as the reference.

| | PV reconnection | RSPV-LA Heterogeneity | RSPV-LA Ablation Gaps | AF Inducibility | RF Lesion Size | Iron Stain |
|---|---|---|---|---|---|---|
| 4 weeks after ablation | ↓↓ | ↓↓ | ↓↓ | ↓↓ | ↑ | =/↑ |

Example 3

Heat Shock Protein Inhibition Will Increase Lesion Volumes in a Rodent Model of Radiofrequency Ablation Introduction.

Thermal injury leads to up-regulation of protective cellular pathways, mediated by heat shock proteins (HSPs), which can render myocardial tissues resistant to subsequent heat exposure.

Methods.

Using an open-chest rodent survival model and a custom-made catheter, RF was applied to the epicardium at 3 W for 20 seconds after infusion of a HSP inhibitor, intravenous quercetin (n=20, 10 mg/kg), or control (n=20). Animals were sacrificed at 1 (n=10 each) and 24 hours (n=10 each) after ablation. RFA lesions were stained and analyzed under microscopy.

Results.

RFA after HSP inhibition with IV quercetin did not acutely result in larger ablation lesions analyzed at 1 hour after RFA. However, if lesions were assessed 24 hours after ablation, RFA after HSP inhibition resulted in larger lesion volumes, (37.6±10.5 vs 25.7±8.6 µl; p=0.01) and greater lesion depth (1.8±0.3 vs 1.3±0.3 mm; p=0.01). Initial impedances, impedance drops, and peak temperatures were not different (Table 8). Microscopy demonstrated lesions with larger necrotic cores and border zones in quercetin-treated animals compared to controls. No adverse events related to HSP inhibition were noted.

Conclusion.

HSP inhibition during RFA in a rodent survival model demonstrated larger ablation lesions after 24 hours, consistent with its physiologic target. This strategy may have clinical implications for improving RF ablation outcomes with improved lesion maturation and reduced cardiomyocyte dormancy induced by HSPs.

TABLE 8

Table of ablation parameters, 24 hours after RFA, for IV quercetin vs. control.

| | N | Watts | Lesion Depth (mm) | Volume (ul) | Initial Impedance | Impedance Drop | Peak temp |
|---|---|---|---|---|---|---|---|
| Control | 10 | 3 W | 1.3 ± 0.3 | 25.7 ± 8.6 | 487 ± 152 | 326 ± 141 | 70 ± 9 |
| Quercetin | 10 | 3 W | 1.8 ± 0.3 | 37.6 ± 10.5 | 597 ± 123 | 401 ± 105 | 75 ± 8 |
| p value | | | p = 0.01 | p = 0.01 | p = 0.1 | p = 0.19 | p = 0.17 |

REFERENCES

All publications, patent applications, patents, and other references mentioned in the specification are indicative of the level of those skilled in the art to which the presently disclosed subject matter pertains. All publications, patent applications, patents, and other references (e.g., websites, databases, etc.) mentioned in the specification are herein incorporated by reference in their entirety to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Antonio E L, Dos Santos A A, Araujo S R, Bocalini D S, Dos Santos L, Fenelon G, Franco M F, Tucci P J. Left ventricle radio-frequency ablation in the rat: A new model of heart failure due to myocardial infarction homogeneous in size and low in mortality. *J Card Fail.* 2009; 15:540-548

Bañobre-López M, Teijeiro A, Rivas J. Magnetic nanoparticle-based hyperthermia for cancer treatment. *Rep Pract Oncol Radiother.* 2013; 18:397-400

Bassen H, Kainz W, Mendoza G, Kellom T. Mri-induced heating of selected thin wire metallic implants—laboratory and computational studies—findings and new questions raised. *Minim Invasive Ther Allied Technol.* 2006; 15:76-84

Burke M C, Kopp D E, Alberts M, Patel A, Lin A C, Kall J G, Arruda M, Mazeika P, Wilber D J. Effect of radiofrequency current on previously implanted pacemaker and defibrillator ventricular lead systems. *J Electrocardiol.* 2001; 34 Suppl:143-148

Cardinal J, Klune J R, Chory E, Jeyabalan G, Kanzius J S, Nalesnik M, Geller D A. Noninvasive radiofrequency ablation of cancer targeted by gold nanoparticles. *Surgery.* 2008; 144:125-132

Cho S K, Emoto K, Su L J, Yang X, Flaig T W, Park W. Functionalized gold nanorods for thermal ablation treatment of bladder cancer. *J Biomed Nanotechnol.* 2014; 10:1267-1276

Ding C, Gepstein, L, Duy Nguyen, Emily Wilson, George Hulley, Randall Lee, Andrew Beaser, and Jeffrey Olgin. High resolution optical mapping of ventricular tachycardia in rats with chronic myocardial infarction.

Gabai V L, Yaglom J A, Volloch V, Meriin A B, Force T, Koutroumanis M, Massie B, Mosser D D, Sherman M Y. Hsp72-mediated suppression of c-jun n-terminal kinase is implicated in development of tolerance to caspase-independent cell death. *Mol Cell Biol.* 2000; 20:6826-6836

Gerstenfeld E P, Michele J. Pulmonary vein isolation using a compliant endoscopic laser balloon ablation system in a swine model. *J Interv Card Electrophysiol.* 2010; 29:1-9

Gordon A N, Granai C O, Rose P G, Hainsworth J, Lopez A, Weissman C, Rosales R, Sharpington T. Phase ii study of liposomal doxorubicin in platinum- and paclitaxel-refractory epithelial ovarian cancer. *J Clin Oncol.* 2000; 18:3093-3100

Haines D. Biophysics of ablation: Application to technology. *J Cardiovasc Electrophysiol.* 2004; 15: S2-S11

Hansen R K, Oesterreich S, Lemieux P, Sarge K D, Fuqua S A. Quercetin inhibits heat shock protein induction but not heat shock factor dna-binding in human breast carcinoma cells. *Biochem Biophys Res Commun.* 1997; 239: 851-856

Lakkireddy D, Patel D, Ryschon K, Bhateja R, Bhakru M, Thal S, Verma A, Wazni O, Kilicaslan F, Kondur A, Prasad S, Cummings J, Belden W, Burkhardt D, Saliba W, Schweikert R, Bhargava M, Chung M, Wilkoff B, Tchou P, Natale A. Safety and efficacy of radiofrequency energy catheter ablation of atrial fibrillation in patients with pacemakers and implantable cardiac defibrillators. *Heart Rhythm.* 2005; 2:1309-1316

Lammers W J, Schalij M J, Kirchhof C J, Allessie M A. Quantification of spatial inhomogeneity in conduction and initiation of reentrant atrial arrhythmias. *Am J Physiol.* 1990; 259:H1254-1263

Leask A. Tgfβ, cardiac fibroblasts, and the fibrotic response. *Cardiovascular Research.* 2007; 74:207-212

Lee Y J, Erdos G, Hou Z Z, Kim S H, Kim J H, Cho J M, Corry P M. Mechanism of quercetin-induced suppression and delay of heat shock gene expression and thermotolerance development in ht-29 cells. *Mol Cell Biochem.* 1994; 137:141-154

Liu Y, Wu X, Zhou H, Liu X, Zhang F, Yang J. The fluorescence enhancement of quercetin-nucleic acid system and the analytical application. *Luminescence.* 2009; 24:416-421

Martinelli V, Cellot G, Toma F M, Long C S, Caldwell J H, Zentilin L, Giacca M, Turco A, Prato M, Ballerini L, Mestroni L. Carbon nanotubes instruct physiological growth and functionally mature syncytia: Nongenetic engineering of cardiac myocytes. *ACS Nano.* 7:5746-5756

Nakagawa H, Yamanashi W S, Pitha J V, Arruda M, Wang X, Ohtomo K, Beckman K J, McClelland J H, Lazzara R, Jackman W M. Comparison of in vivo tissue temperature profile and lesion geometry for radiofrequency ablation with a saline-irrigated electrode versus temperature control in a canine thigh muscle preparation. *Circulation.* 1995; 91:2264-2273

Nguyen D T, Barham W, Moss J, Zheng L, Shillinglaw B, Quaife R, Tzou W S, Sauer W H. Gadolinium augmentation of myocardial tissue heating during radiofrequency ablation. *J Amer Coll Cardiol:* Clin EP 2015; 1:177-184

Nguyen D T, Barham W, Zheng L, Dinegar S, Tzou W S, Sauer W H. Effect of radiofrequency energy delivery in proximity to metallic medical device components. *Heart Rhythm.* 2015 (in press)

Nguyen D T, Barham W, Zheng L, Dinegar S, Tzou W S, Sauer W H. Effect of radiofrequency energy delivery in proximity to metallic medical device components. *Heart Rhythm.* 2015

Nguyen D T, Barham W, Zheng L, Shillinglaw B, Tzou W S, Neltner B, Mestroni L, Bosi S, Ballerini L, Prato M, Sauer W H. Carbon nanotube facilitation of myocardial ablation with radiofrequency energy. *J Cardiovasc Electrophysiol.* 2014; 25:1385-1390

Nguyen D T, Ding C, Wilson E, Marcus G M, Olgin J E. Pirfenidone mitigates left ventricular fibrosis and dysfunction after myocardial infarction and reduces arrhythmias. *Heart Rhythm.*

Nguyen D T, Moss J D, Zheng L, Huang J, Barham W, Sauer W H. Effects of radiofrequency energy delivered through partially insulated metallic catheter tips on myocardial tissue heating and ablation lesion characteristics. *Heart Rhythm.* 2015; 12:623-630

Nguyen D T, Olson M, Zheng L, Barham W, Moss J D, Sauer W H. Effect of irrigant characteristics on lesion formation after radiofrequency energy delivery using ablation catheters with actively cooled tips. *J Cardiovasc Electrophysiol.* 2015

Olson M D, Phreaner N, Schuller J L, Nguyen D T, Katz D F, Aleong R G, Tzou W S, Sung R, Varosy P D, Sauer W H. Effect of catheter movement and contact during application of radiofrequency energy on ablation lesion characteristics. *J Interv Card Electrophysiol.* 38: 123-129

Polla B S, Kantengwa S, François D, Salvioli S, Franceschi C, Marsac C, Cossarizza A. Mitochondria are selective targets for the protective effects of heat shock against oxidative injury. *Proc Natl Acad Sci USA.* 1996; 93:6458-6463

Rejinold N S, Jayakumar R, Kim Y C. Radio frequency responsive nano-biomaterials for cancer therapy. *J Control Release.* 2015; 204:85-97

Rivera E, Valero V, Arun B, Royce M, Adinin R, Hoelzer K, Walters R, Wade J L, Pusztai L, Hortobagyi G N. Phase ii study of pegylated liposomal doxorubicin in combination with gemcitabine in patients with metastatic breast cancer. *J Clin Oncol.* 2003; 21:3249-3254

Sacher F, Cochet H. After the fire and ice age, are we entering the metal age? *J Amer Coll Cardiol: Clin EP.* 2015; 1:185-186

Salama G, Kanai A, Efimov I R. Subthreshold stimulation of purkinje fibers interrupts ventricular tachycardia in intact hearts. Experimental study with voltage-sensitive dyes and imaging techniques. *Circ Res.* 1994; 74:604-619

Thériault JR, Adachi H, Calderwood S K. Role of scavenger receptors in the binding and internalization of heat shock protein 70. *J Immunol.* 2006; 177:8604-8611

Xanthoudakis S, Nicholson D W. Heat-shock proteins as death determinants. *Nat Cell Biol.* 2000; 2:E163-165

Xiao J W, Fan S X, Wang F, Sun L D, Zheng X Y, Yan C H. Porous pd nanoparticles with high photothermal conversion efficiency for efficient ablation of cancer cells. *Nanoscale.* 2014; 6:4345-4351

Yang W, Ahmed M, Tasawwar B, Levchenko T, Sawant R R, Collins M, Signoretti S, Torchilin V, Goldberg S N. Radiofrequency ablation combined with liposomal quercetin to increase tumour destruction by modulation of heat shock protein production in a small animal model. *Int J Hyperthermia.* 2011; 27:527-538

Yu L, Scherlag B J, Dormer K, Nguyen K T, Pope C, Fung K-M, Po S S. Autonomic denervation with magnetic nanoparticles. *Circulation.* 2010; 122:2653-2659

Zhang Y, Takagawa J, Sievers R E, Khan M F, Viswanathan M N, Springer M L, Foster E, Yeghiazarians Y. Validation of the wall motion score and myocardial performance indexes as novel techniques to assess cardiac function in mice after myocardial infarction. *Am J Physiol Heart Circ Physiol.* 2007; 292:H1187-1192

Zhao H, Li G L, Wang R Z, Li S F, Wei J J, Feng M, Zhao Y J, Ma W B, Yang Y, Li Y N, Kong Y G. A comparative study of transfection efficiency between liposomes, immunoliposomes and brain-specific immunoliposomes. *J Int Med Res.* 2010; 38:957-966

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for augmenting radiofrequency ablation of a target cardiac tissue in a subject in need thereof, the method comprising:
   (a) administering an effective amount of a composition comprising metallic nanoparticles to the subject;
   (b) using a magnetic field to guide the metallic nanoparticles to the target cardiac tissue to be ablated in the subject; and
   (c) applying a radiofrequency energy to the target cardiac tissue and the metallic nanoparticles guided to the target cardiac tissue, thereby augmenting radiofrequency ablation of the target cardiac tissue in the subject.

2. The method of claim 1, wherein the metallic nanoparticles are selected from the group consisting of copper nanoparticles, gadolinium nanoparticles, gold nanoparticles, iron nanoparticles, titanium nanoparticles, and combinations thereof.

3. The method of claim 1, wherein the metallic nanoparticles are encapsulated by liposomes.

4. The method of claim 1, wherein the composition further comprises an agent that decreases an expression level of a heat shock protein and/or activity of a heat shock protein.

5. The method of claim 1, wherein the magnetic field generates a pull force of between 0.001 and 1000 pounds force.

6. The method of claim 5, wherein the magnetic field is placed adjacent to the target cardiac tissue to be ablated.

7. The method of claim 6, wherein the magnetic field guides the metallic nanoparticles to the target cardiac tissue to be ablated.

8. The method of claim 1, further comprising imaging the metallic nanoparticles in the subject.

9. The method of claim 1, further comprising administering an effective amount of at least one prophylactic agent to the subject to reduce the risk and/or severity of an adverse reaction to the composition administered to the subject.

10. A method for augmenting electrical ablation of a target cardiac tissue in a subject in need thereof, the method comprising:
    (a) administering an effective amount of a composition comprising metallic nanoparticles to the subject;
    (b) using a magnetic field to guide the metallic nanoparticles to the target cardiac tissue to be ablated in the subject; and
    (c) applying electrical energy to the target cardiac tissue and the metallic nanoparticles guided to the target cardiac tissue, thereby heating the metallic nanoparticle and augmenting electrical ablation by increasing ablation lesion size of the target cardiac tissue in the subject.

11. The method of claim 10, wherein the metallic nanoparticles are selected from the group consisting of copper nanoparticles, gadolinium nanoparticles, gold nanoparticles, iron nanoparticles, titanium nanoparticles, and combinations thereof.

12. The method of claim 10, wherein the metallic nanoparticles are encapsulated by liposomes.

13. The method of claim 10, wherein the composition further comprises an agent that decreases an expression level and/or activity of a heat shock protein.

14. The method of claim 10, wherein the magnetic field generates pull force of between 0.001 and 1000 pounds force.

15. The method of claim 14, wherein the magnetic field is placed adjacent to the target cardiac tissue to be ablated.

16. The method of claim 15, wherein the magnetic field guides the metallic nanoparticles to the target cardiac tissue to be ablated.

17. The method of claim 10, further comprising imaging the metallic nanoparticles in the subject.

18. The method of claim 10, further comprising administering an effective amount of at least one prophylactic agent to the subject to reduce the risk and/or severity of an adverse reaction to the composition administered to the subject.

* * * * *